(12) United States Patent
Sampath

(10) Patent No.: US 9,545,420 B2
(45) Date of Patent: Jan. 17, 2017

(54) METHOD OF PROMOTING WOUND HEALING

(71) Applicant: Agency for Science, Technology and Research, Singapore (SG)

(72) Inventor: Prabha Sampath, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/417,763

(22) PCT Filed: Jul. 29, 2013

(86) PCT No.: PCT/SG2013/000316
§ 371 (c)(1),
(2) Date: Jan. 27, 2015

(87) PCT Pub. No.: WO2014/017987
PCT Pub. Date: Jan. 30, 2014

(65) Prior Publication Data
US 2015/0290289 A1    Oct. 15, 2015

(30) Foreign Application Priority Data

Jul. 27, 2012    (SG) .................................. 201205614

(51) Int. Cl.
*A61K 48/00*    (2006.01)
*C07H 21/02*    (2006.01)
(Continued)

(52) U.S. Cl.
CPC ....... *A61K 31/7088* (2013.01); *A61K 38/1709* (2013.01); *C12N 15/1136* (2013.01); *C12N 2310/113* (2013.01); *C12N 2310/14* (2013.01); *C12N 2310/315* (2013.01); *C12N 2310/322* (2013.01); *C12N 2310/3231* (2013.01); *C12N 2320/31* (2013.01)

(58) Field of Classification Search
USPC ........................................... 514/44; 536/24.5
See application file for complete search history.

(56) References Cited

U.S. PATENT DOCUMENTS 7,943,756 B2 *   5/2011   Tuschl ................. C12N 15/113
                                                   435/325
2009/0291907 A1   11/2009   Esau et al.

FOREIGN PATENT DOCUMENTS

WO   WO-2006/137941   12/2006
WO   WO-2014/017987   1/2014

OTHER PUBLICATIONS

"International Application No. PCT/SG2013/000316, International Search Report and Written Opinion dated Sep. 19, 2013", (Sep. 19, 2013), 12 pgs.

(Continued)

*Primary Examiner* — Terra C Gibbs
(74) *Attorney, Agent, or Firm* — Schwegman Lundberg & Woessner, P.A.

(57) ABSTRACT

Disclosed is a method of promoting wound healing or wound closure. The method comprises administration of a miR-198 inhibitor and/or a follistatin-like-1 (FSTL1) polypeptide. Also disclosed are method of treating chronic cutaneous wounds, method of identifying a non-healing wound, use and a pharmaceutical composition comprising a miR-198 inhibitor and/or a follistatin-like-1 (FSTL1) polypeptide.

14 Claims, 15 Drawing Sheets

(51) Int. Cl.
  C07H 21/04    (2006.01)
  C12N 15/11    (2006.01)
  A61K 31/7088  (2006.01)
  A61K 38/17    (2006.01)
  C12N 15/113   (2010.01)

(56) References Cited

OTHER PUBLICATIONS

Pastar, Irena, et al., "Attenuation of the transforming growth factor beta-signaling pathway in chronic venous ulcers", Mol Med. Mar. 2010;16(3-4):92-101, (Mar. 2010), 92-101.

Sundaram, Gopinath M., et al., "'See-saw' expression of microRNA-198 and FSTL1 from a single transcript in wound healing", Nature, vol. 495, Mar. 7, 2013, 103-106, (Mar. 7, 2013), 103-106.

"European Application Serial No. 13822123.9, Supplementary Partial European Search Report mailed Feb. 19, 2016", 10 pgs.

Blakytny, R., et al., "The molecular biology of chronic wounds and delayed healing in diabetes". *Diabetic Medicine*, 23(6), (2006), 594-608.

Caldwell, Emily, "Secret to Healing Chronic Wounds Might Lie in Tiny Pieces of Silent RNA", [online]. [archived on Apr. 27, 2012]. Retrieved from the Internet: <URL: http://web.archive.org/web/20120427121217/http://researchnews.osu.edu/archive/mir210wounds.htm>, (2012), 3 pgs.

Chan, Yuk C., et al., "mIR-210:: The Master Hypoxamir", *Microcirculation*, 19(3), (2012), 215-223.

Felder, Marcel, et al., "Microfluidic wound-healing assay to assess the regenerative effect of HGF on wounded alveolar epithelium", *Lab on a Chip*, 12(3), (2012), 640-646.

Geng, Yan, et al., "Follistatin-like 1 (Fstl1) is a bone morphogenetic protein(BMP) 4 signaling antagonist in controlling mouse lung development", *Proc. Natl. Acad. Sci. USA*, 108(17), (2011), 7058-7063.

Penn, Jack W., et al., "The role of the TGF-$\beta$ family in wound healing, burns and scarring: a review", *Int J Burn Trauma*, 2(1), (2012), 18-28.

Sung, Tzu-Ling, et al., "miR-198 Inhibits HIV-1 Gene Expression and Replication in Monocytes and Its Mechanism of Active Appears to Involve Repression Pathogens of Cyclin T1", *PLOS Pathogens*, 5(1), (2009), 1-13.

"Singapore Application No. 11201500615W, Written Opinion dated Sep. 18, 2015", (Sep. 18, 2015), 7 pgs.

Tan, Sheng, et al., "miR-198 inhibits migration and invasion of hepatocellular carcinoma cells by targeting the HGF/c-MET pathway", FEBS Letters 585 (2011) 2229-2234, (Jun. 7, 2011), 2229-2234.

"European Application Serial No. 13822123.9, extended European Search Report mailed Jul. 29, 2016", 20 pgs.

Harrison, C. A., et al., "Antagpnists of activin signalling: mechanisms and potential biological applications", *Trends in Endocrinology and Metabolism*, 16(2), (Mar. 2005), 73-78.

Lara-Pezzi, Enrique, et al., "Expression of Follistatin-Related Genes Is Altered in Heart Failure", *Endocrinology*, 149(11), (2008), 5822-5827.

Wankell, M., et al., "The activin binding proteins follistatin and follistatin-related protein are differentially regulated in vitro and during cutaneous wound repair", *Journal of Endocrinology*, 171(3), (2001), 385-395.

* cited by examiner

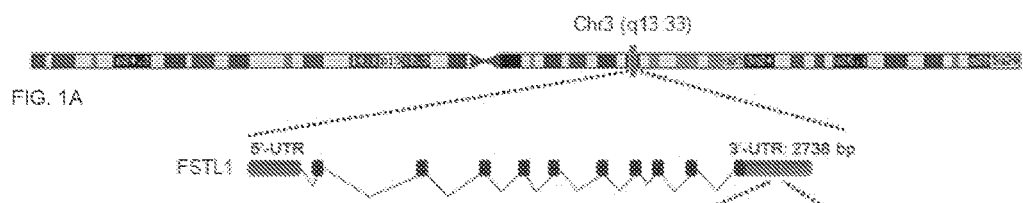
FIG. 1A
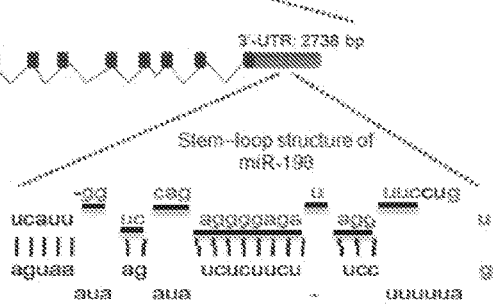
FIG. 1B
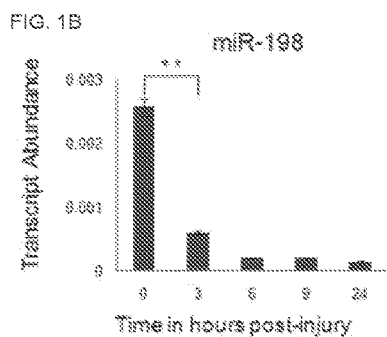
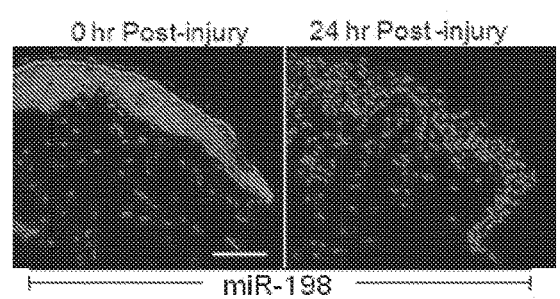
FIG. 1C
FIG. 1D
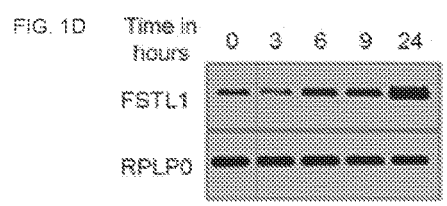
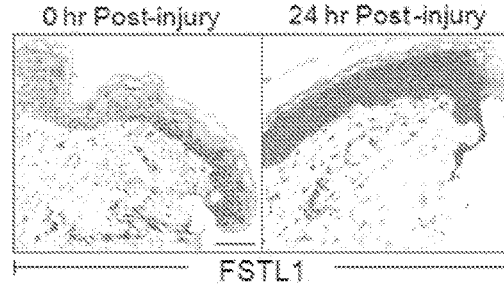
FIG. 1E

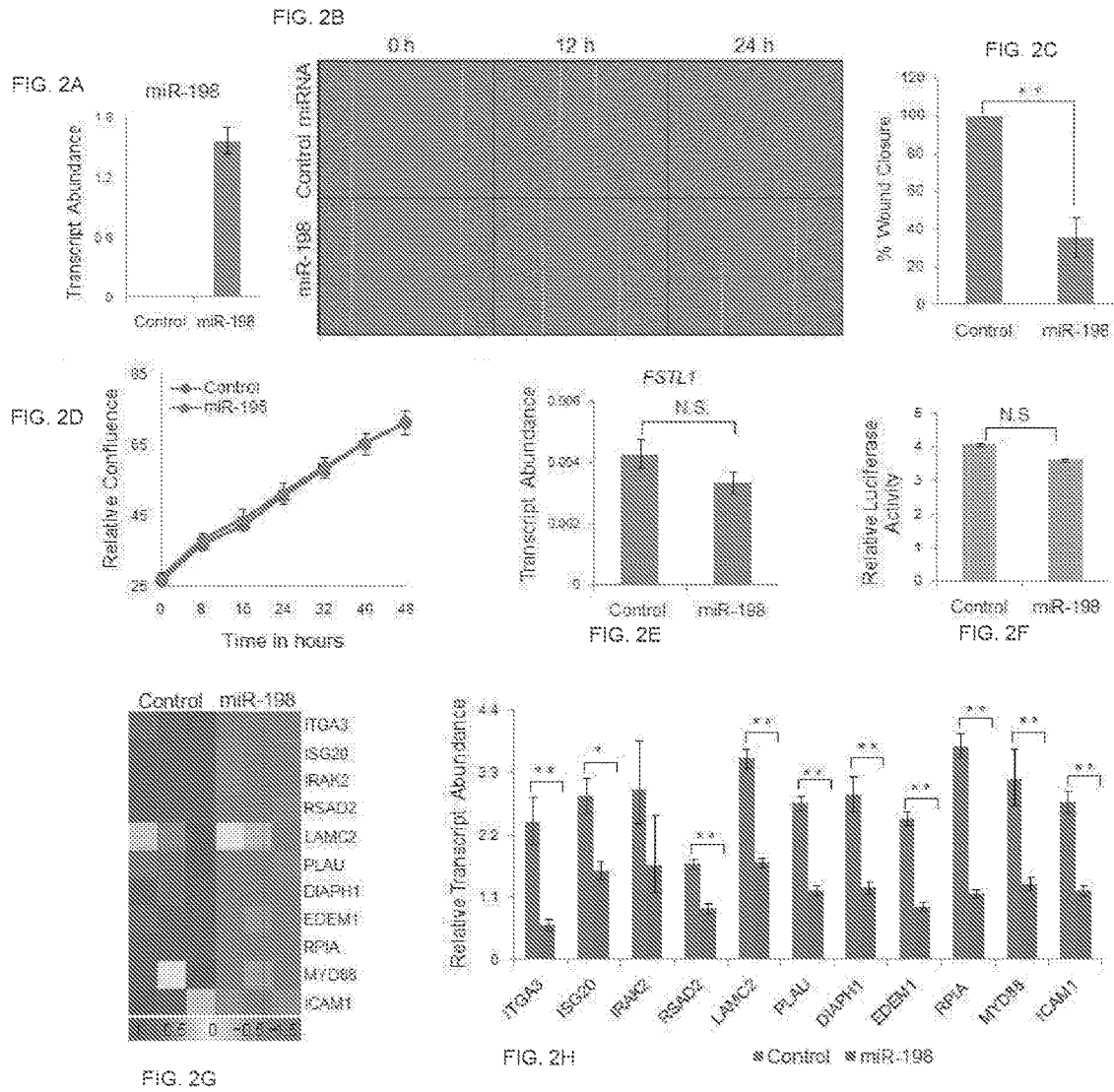

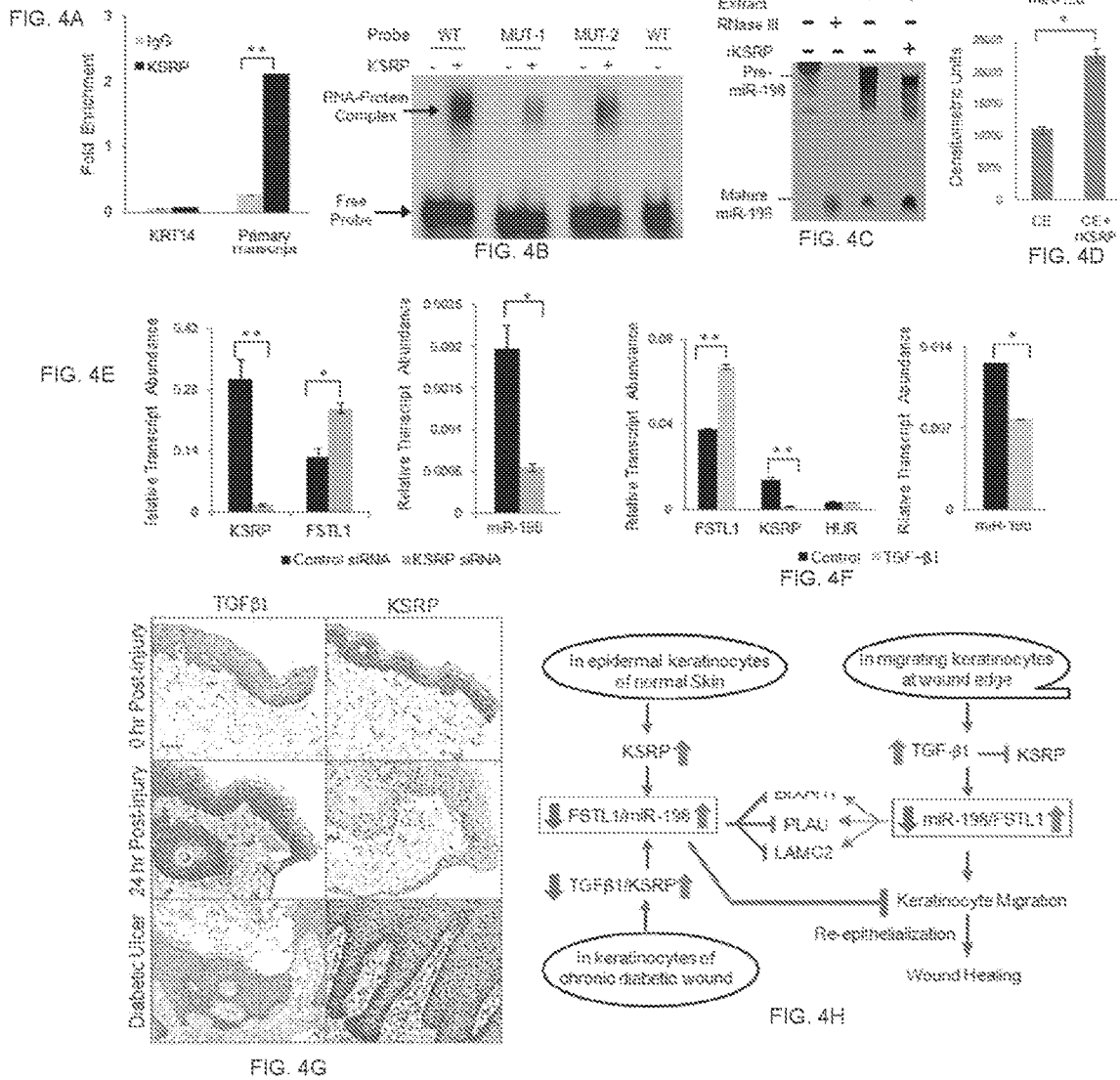

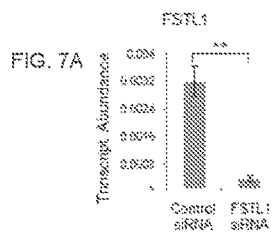
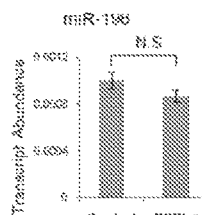
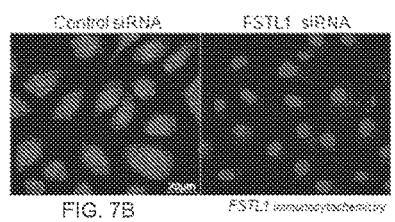
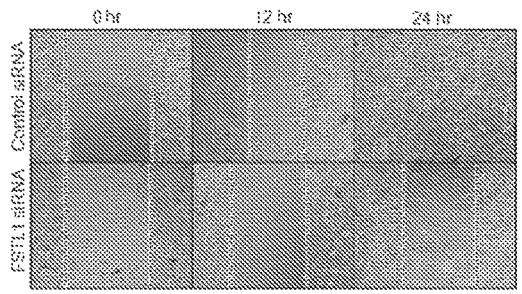
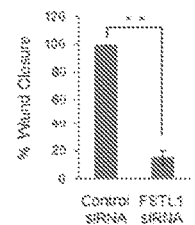
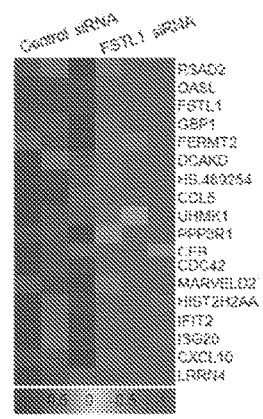
FIG. 7A, FIG. 7B, FIG. 7C, FIG. 7D, FIG. 7E, FIG. 7F
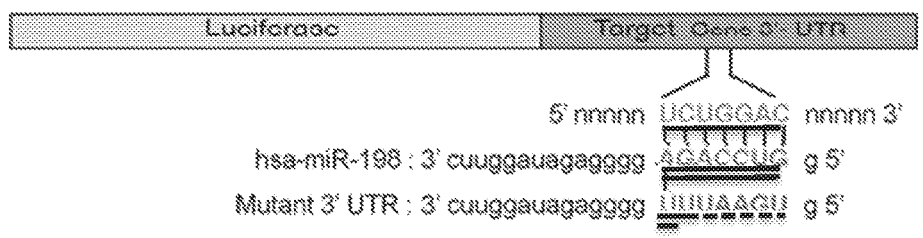
FIG. 8

Pre miR-198 WT- 5' TCATTGGTCC AGAGGGAGA TAGGTTCCTG TGATTTTTCC TTCTTCTCTA TAGAATAAAT GA 3'
Pre miR-198 M1- 5' TCATTGGTCC AGAGGGAGA TAGGTTCCTG TCATTTTTCC TTCTTCTCTA TAGAATAAAT GA 3'
Pre miR-198 M2- 5' TCATTGGTCC AGAGGGAGA TACCTTCCTG TGATTTTTCC TTCTTCTCTA TAGAATAAAT GA 3'

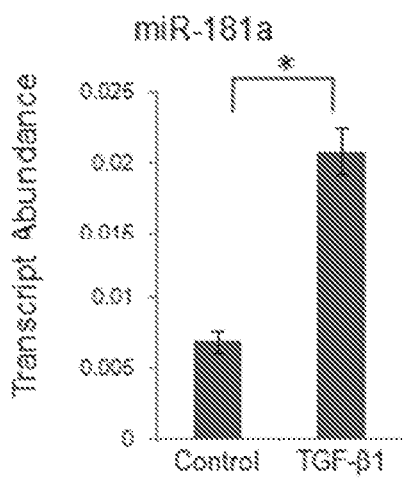
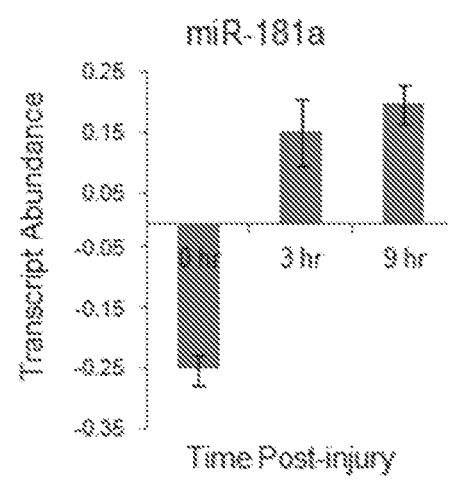
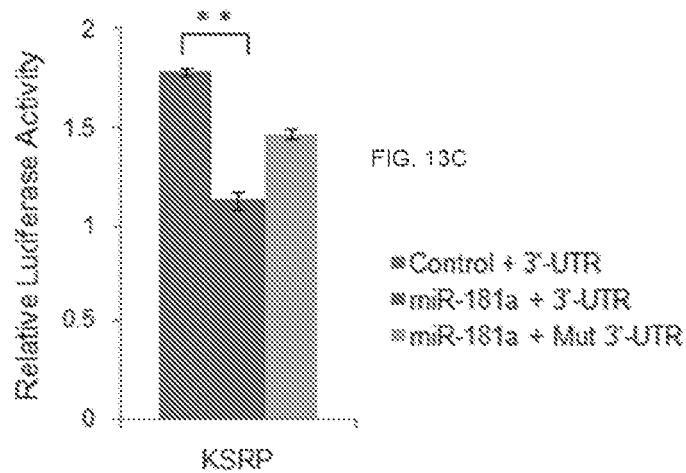
FIG. 13A
FIG. 13B
FIG. 13C

PLAU

LAMC2

DIAPH1

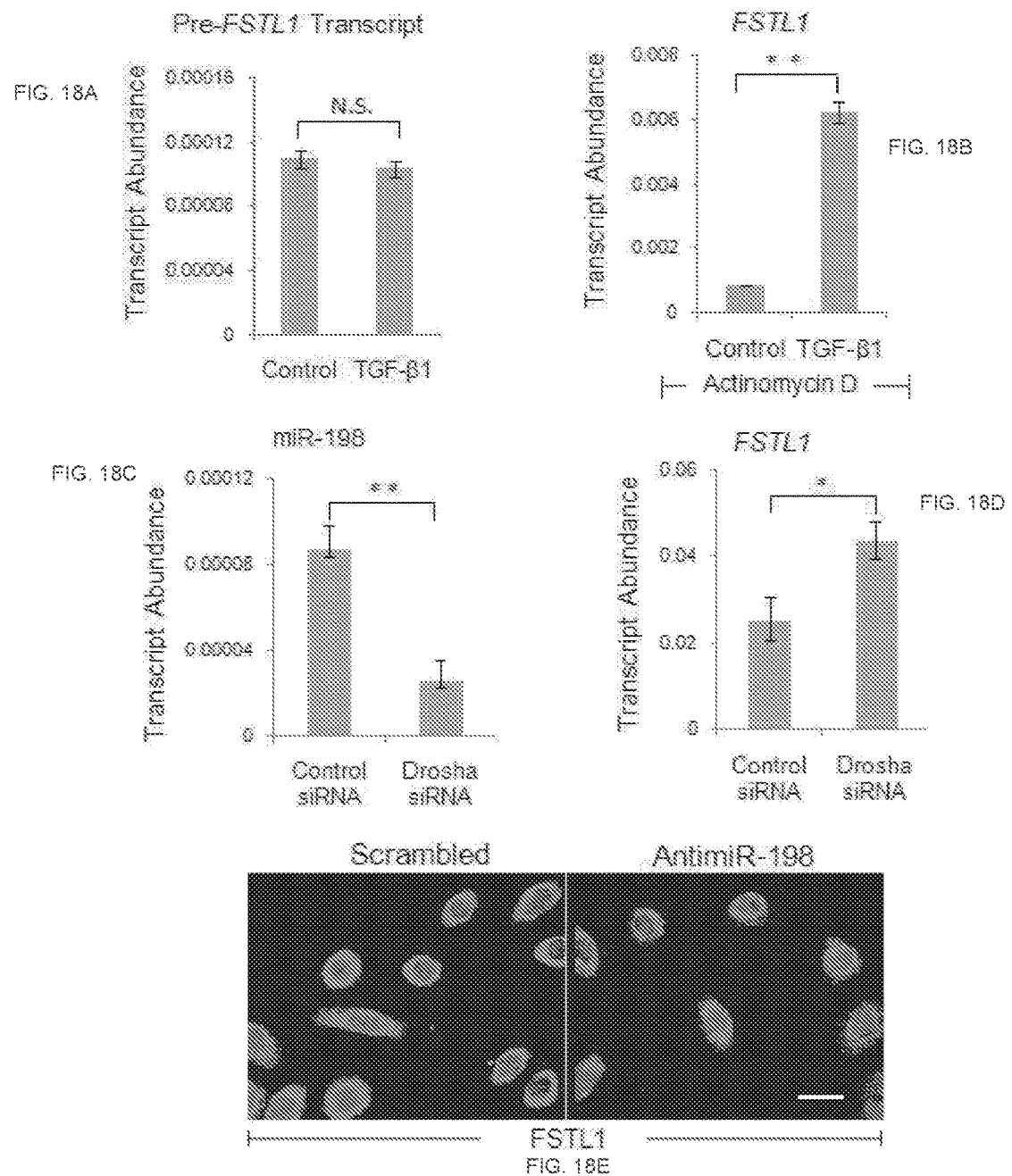

METHOD OF PROMOTING WOUND HEALING

CROSS-REFERENCE TO RELATED APPLICATIONS

This application is a U.S. national stage application filed under 35 U.S.C. §371 from International Application Serial No. PCT/SG2013/000316, which was filed Jul. 29, 2013, and published as WO 2014/017987 on Jan. 30, 2014, and which claims the benefit of priority of SG patent application No. 201205614-9, filed 27 Jul. 2012, which applications and publication are incorporated by reference as if reproduced herein and made a part hereof in their entirety, and the benefit of priority of each of which is claimed herein.

FIELD OF THE INVENTION

The present invention generally relates to the field of biochemistry. In particular, the present invention relates to mi-RNAs, anti-miRNAs and polypeptides; which can be used for the treatment of wounds.

BACKGROUND OF THE INVENTION

Diabetes is a group of diseases characterized by a high glucose level in blood that is caused by the subject's impaired ability to produce and/or use insulin. When diabetes is not well managed, diabetes can deteriorate steadily and cause complications such as blindness, nerve damage, kidney failure, heart disease and limb amputation. Many of these complications are due to damage to vasculature and the inability to heal wounds. Chronic wounds caused by diabetic patient's inability to heal wounds are a major global health burden and the most common cause of lower extremity amputations. In extreme cases, ineffective wound healing can lead to death.

Wound healing requires an orchestrated integration of complex biological events including cell migration, proliferation and extracellular remodeling with matrix deposition, globally stimulated by TGF-β and other growth factors. In diabetes, these complex and interactive protective processes are disturbed. Accordingly, there is a need to provide a method or composition that can restore or improve normal wound healing.

SUMMARY OF THE INVENTION

In one aspect, there is provided a method of promoting wound healing or wound closure. The method as described herein comprises administration of a miR-198 inhibitor and/or follistatin-like-1 (FSTL1) polypeptide.

In another aspect, there is provided a method of treating chronic cutaneous wounds. The method of treating chronic cutaneous wounds may comprise the administration of a miR-198 inhibitor and/or follistatin-like-1 (FSTL1) polypeptide.

In another aspect, there is provided a method of identifying a non-healing wound (chronic cutaneous wound). The method of identifying the chronic cutaneous wound may comprise analyzing expression level of miR-198, wherein expression or an increased expression of miR-198 indicates that the wound is a chronic cutaneous wound. The method of identifying a non-healing wound as described herein may optionally comprise analyzing expression of FSTL1 gene and/or FSTL1 polypeptide level, wherein reduced or non-expression of FSTL1 gene and/or reduced level or absence of FSTL1 polypeptide indicates that the wound is a chronic cutaneous wound.

In another aspect, there is provided a use of miR-198 as a biomarker for identifying a non-healing wound (chronic cutaneous wound).

In another aspect, there is provided a use of miR-198 in the manufacture of a medicament for treating non-healing wound. Also provided is a use of FSTL1 polypeptide in the manufacture of a medicament for treating a non-healing wound.

In another aspect, there is provided a pharmaceutical composition comprising the compositions or compounds as described herein. The pharmaceutical composition may comprise a miR-198 inhibitor and TGF-β1; or the miR-198 inhibitor and a FSTL1 polypeptide; or the FSTL polypeptide and TGF-β1; or the miR-198 inhibitor and TGF-β1 and the FSTL1 polypeptide.

BRIEF DESCRIPTION OF THE DRAWINGS

The invention will be better understood with reference to the detailed description when considered in conjunction with the non-limiting examples and the accompanying drawings, in which:

FIG. 1 shows the expression of an exonic miRNA or linked ORF in context-specific physiological states. a) Schematic of FSTL1 gene in chromosome 3 (NCBI Reference Sequence: NM_007085), showing the exon-intron boundaries, the 3'-UTR sequence encoding the miR-198 precursor (nucleotides which are underlined indicate the mature miR-198; SEQ ID NO:4) b) Bar graph of showing miR-198 expression as assayed by qRT-PCR in organ culture explants at indicated time points after injury. Significant down-regulation of miR-198 observed as early as 3 hours post-injury **[P<0.001]. c) Images obtained from in situ hybridization with LNA probes specific for mature miR-198 on normal skin at (left) 0 and (right) 24 hours after injury. Note, a marked down-regulation of miR-198 expression at 24 hours after wounding. d) Representative semi-quantitative-RT-PCR analysis of FSTL1 mRNA in explant samples before and after injury at indicated time points. e) Immunohistochemical localization of FSTL1 protein at (left) 0 and (right) 24 hours after wounding. FSTL1 protein expression is observed at 24 hours after wounding (n=5). Scale bar=100 µM. FIG. 1 demonstrates differential miRNA expression profile of human skin ex vivo organ culture system at 0 and 24 hours post-injury. FIG. 1 demonstrates that miR-198 is a consistent and significant differentially-expressed miRNA that is down-regulated upon injury.

FIG. 2 a) shows histogram representing quantification of mature miR-198 in N/TERT-1 cells transfected with a control or miR-198 (n=3). b) shows representative images of migrating keratinocytes transfected with non-targeting miRNA control (upper panel) or miR-198 (lower panel) at different time-points after scratch wounding. Dotted lines mark the migrating edge of the keratinocyte cellsheet (n=6). c) shows histogram representing relative wound closure in the scratch wound assay. By 24 hours, complete wound closure was observed in control transfected cells, while over-expression of miR-198 resulted in 35±10% wound closure (n=6). **P<0.001. Error bars represent standard deviation. d) shows proliferation of keratinocytes transfected with control or miR-198 assessed by relative cell confluence. Over-expression of miR-198 was not associated with any significant difference in proliferation (n=3). e) shows relative levels of FSTL1 mRNA in N/TERT-1 cells transfected with control or miR-198 mimic. N.S: not significant (n=3). miR-198 over expression did not result in a significant change in FSTL1 mRNA levels. f) shows cells were co-transfected with FSTL1 3'-UTR luciferase reporter constructs either with miR-198 or a non-targeting, scrambled control. Normalized relative luciferase activities are shown a sa bar diagram. Luciferase activity is expressed as the mean relative to controls N.S: not significant (n=3). g) shows gene expression values of selected genes from microarray data of keratinocytes transfected with control or miR-198, represented as a heat-map. Expression values displayed as shades relative to the individual mean value of the gene in a linear scale. h) shows histogram representing relative transcript abundances (control versus miR-198 overexpression) of selected genes identified from microarrays and validated by qRT-PCR (n=3). Microarray data shows significant correlation with qRT-PCR results. *P<0.05, **P<0.001. Student's t-test was used to calculate P value and error bars denote mean±s.e.m. Thus, FIG. 2 shows miR-198 inhibition of keratinocyte migration is independent of FSTL1.

FIG. 4 shows a series of assays conducted to understand the regulation of the post-transcriptional switch that determines the fate of a transcript to function as a pri-miRNA or a mRNA. a) shows RNA immunoprecipitations from keratinocyte lysates using anti-KSRP antibody or IgG control either in the presence or absence of TGF-β1. Quantitative RT-PCR representing fold enrichment of transcripts reveals specific binding of KSRP to pri-miR-198 transcript but not to the most abundant mRNA species, KRTI4 (n=3). b) shows RNA-gel retardation assay shows specific binding of KSRP to the G-rich motif in the loop of pre-miR-198 transcript and abrogation of binding with a mutant CUC motif in this site (Mut-1). Mutation of GG motif in the stem of the pre-miR-198 transcript to CC results only in a modest loss of binding (Mut-2). RNA-protein complex was observed only with KSRP, not with a BSA control (last lane) (n=3). c) shows efficient processing of pre-miR-198 in the presence of recombinant KSRP (rKSRP). In vitro synthesized pre-miR-198 transcripts were incubated with 293T cytoplasmic extract in the absence or presence of increasing concentration of rKSRP. Cleaved mature miR-198 was detected by co-migration with the product released when pre-miR-198 was treated with RNase III. d) shows histogram representing densitometric quantification of the mature miR-198 *P<0.05. e) shows histogram representing relative transcript abundance in keratinocytes transfected with control siRNA or siRNA against KSRP. Note increase in FSTL1 mRNA and a corresponding decrease in mature miR-198 with the knock-down of KSRP. f) shows histogram representing relative transcript abundance in keratinocytes treated with TGF-β1 or control. Treatment with TGF-β1 promotes FSTL1 but inhibits KSRP and miR-198 expression. Expression of HUR is not affected (*[P<0.05], **[P<0.001]). g) shows results of immunohistochemistry with TGF-β1 antibody (left panel) and KSRP antibody (right panel) on normal skin explants and chronic diabetic ulcer sections. h) shows a model depicting post-transcriptional regulon in normal versus chronic diabetic wounds. Scale bar-100 µM. Thus, FIG. 4 shows that KSRP and TGF-β1 regulate the choice between expression of miR-198 or FSTL1.

FIG. 5 shows that FSTL1 transcript can be processed to form mature miR-198 or can function as an FSTL1 mRNA to make FSTL1 protein.

FIG. 6 demonstrates the dynamic expression of miR-198 and FSTL1 at the proximal wound edge 24 hours post-injury.

FIG. 7 a) shows histogram representing FSTL1 transcript abundance in keratinocytes transfected with control non-targeting siRNA or gene-specific siRNA against FSTL1 (n=3) P<0.001. b) shows immunocytochemistry on keratinocytes transfected with gene-specific siRNA against FSTL1 shows down-regulation of FSTL1 protein expression (n=3). c) shows representative images of migrating keratinocytes transfected with a control siRNA or FSTL1-specific siRNA at the indicated time points after scratch wound (n=5). d) shows histograms representing relative wound closure in a scratch wound assay. By 24 hours, complete wound closure was observed in control transfected cells compared to knockdown of FSTL1 leading to 15±5% wound closure (n=5) P<0.001. Error bars represent s.d. e) shows relative expression levels of mature miR-198 in keratinocytes transfected with FSTL1 siRNA compared to control siRNA (N.S=not significant). f) shows gene expression values of selected genes from microarray data of keratinocytes transfected with control non-targeting siRNA or FSTL1 specific siRNA, represented as a heat-map. Expression values displayed in shades of red (low) or blue (high) relative to the individual mean value of the gene in a linear scale. Thus, FIG. 7 shows FSTL1 promotes keratinocyte migration.

FIG. 8 shows the 3' UTR sequences containing miR-198 binding sites are shown (single line) for PLAU (SEQ ID NO:65), DIAPH1 SEQ ID NO:66) and LAMC2 SEQ ID NO:67). For the mutation of miR-198 binding sites in the target 3'UTR, the bases in the seed sequence (double underlined; SEQ ID NO:68)) were mutated to the sequence shown with dotted line SEQ ID NO:69). Mutations were restricted to the conversion of A to Gs and U to Cs and vice versa.

FIG. 9 shows that knock-down of DIAPH1, PLAU and LAMC2 significantly suppressed migration of keratinocytes.

FIG. 10 illustrates that the increased level of miR-198 and absence of FSTL1 protein may be used to identify a wound as a non-healing wound or a chronic cutaneous wound.

FIG. 11 shows KSRP binds to the GUG motif of pre-miR-198 located in the 3'-UTR of FSTL1 mRNA in normal epidermal keratinocytes.

FIG. 12 shows TGF-β1 down-regulates KSRP and facilitates FSTL1 expression.

FIG. 13 a) shows histogram representing relative transcript abundance of miR-181a in keratinocytes treated with TGF-β1 or control. Treatment with TGF-β1 induces miR-181a expression (n=3). b) shows expression of miR-181a in epidermal keratinocytes after injury at indicated time points. c) shows validation of KSRP as a direct target of miR-181a by luciferase reporter assays. Cells were co-transfected with wild type or mutant KSRP 3'-UTR luciferase reporter constructs as indicated, either with miR-181a or non-targeting scrambled control (n=3). Normalized relative luciferase activities are shown as a bar diagram. Luciferase activity is expressed as mean relative to controls. *P<0.05, **P<0.001. Student's t-test was used to calculate P value and error bars denote mean±s.e.m. Thus, FIG. 13 shows KSRP is a target of miR-181a.

FIG. 15 shows FSTL1 mRNA levels upon injury increases over time and not observed in unwounded normal epidermal keratinocytes.

FIG. 16 shows over-expression of targets, in combination can significantly rescue the effect of miR-198 in wound healing.

FIG. 17** shows increase in transcript stability of miR-198 targets upon treatment with TGF-β1.

FIG. 18 a) shows histogram representing relative quantification of pre-FSTL1 transcript detected by primers specifically amplifying the intronic region in keratinocytes treated with TGF-β1 (N.S=non significant) (n=3). b) shows histogram representing relative transcript abundance of FSTL1 in keratinocytes treated with TGF-β1 in the presence of actinomycin D. c) shows histograms showing relative levels of mature miR-198 in keratinocytes transfected with a control siRNA or siRNA specific for human DROSHA (n=3), **P<0.001. d) shows histograms showing relative levels of FSTL1 mRNA in keratinocytes transfected with a control siRNA or siRNA specific for human DROSHA. *P<0.05, P<0.001. Student's t-test was used to calculate P value and error bars denote mean±s.e.m. e) Immunocytochemistry for FSTL1 protein in keratinocytes transfected with control inhibitor or antimiR-198 shows no significant difference in protein levels (n=3). Thus, FIG. 18** shows TGF-β1 facilitates FSTL1 expression.

DETAILED DESCRIPTION OF THE PRESENT INVENTION

Figure 3A:
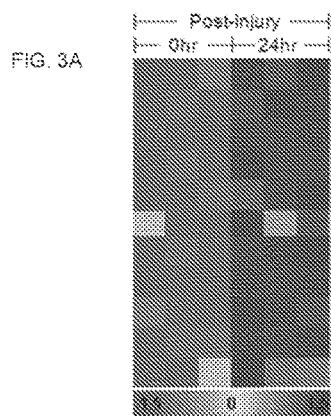
FIG. 3 shows the results of target gene expression in an injury model of human skin organ culture. a) shows heatmap of selected genes (putative targets) generated from microarray using RNA from skin (organ culture) 0 and 24 hours after injury. Expression values are displayed in shades relative to the individual mean value of the gene in a linear scale as a heat-map. b) shows validation of direct targets of miR-198 by luciferase reporter assays. 293T cells were co-transfected with 3'-UTR luciferase reporter constructs as indicated, either with miR-198 or non-targeting scrambled control. Normalized relative luciferase activities are shown as a bar diagram. Luciferase activity is expressed as mean relative to controls. (n=3). **P<0.001. Student's t-test was used to calculate P value and error bars denote mean±s.e.m. c) shows immunohistochemical analysis of miR-198 targets PLAU, LAMC2 and DIAPH1, 0 hour and 24 hours post-injury on sections from organ culture and sections from chronic diabetic wounds. A substantial increase in protein expression of target genes is clearly observed at 24 hours after wounding (middle panel). However in chronic diabetic ulcer wounds (right panel), the expression of target genes remains relatively low (n=8). d) shows FSTL1 protein expression detected by immunohistochemistry (left panel) and in situ hybridization (right panel) for miR-198 on normal wounds 24 hours post-injury or in chronic wound sections (n=8). Scale bar-100 µM. FSTL1 is detected only in. normal wounds but not in chronic diabetic wounds. Chronic diabetic wounds persistently express high levels of miR-198 while miR-198 is down-regulated in normal injury. Thus FIG. 3 demonstrates that the regulatory switch is impaired in chronic wound.

Chronic cutaneous wounds in patients with diabetes mellitus are a major global health burden and the most common cause of lower extremity amputations. Understanding the mechanisms of wound healing could lead to improved therapeutic strategies for accelerating wound closure. It is the aim of the present disclosure to provide methods and compositions for promoting wound healing or wound closure.

As used herein, the term "wound" refers to an injury to the body, including but not limited to an injury from trauma, violence, accident, or surgery. A wound may occur due to laceration or breaking of a membrane (such as the skin) and usually damage to underlying tissues. A wound may occur in a topical location or internally. Chronic wounds may be caused by diseases, including but not limited to diabetes; diseases of internal organs, including but not limited to diseases of the liver, kidneys or lungs; cancer; virus or any other condition that slows the healing process.

Natural healing occurs in clearly defined. stages. Skin wounds of acute nature may heal in 1-3 weeks in a biological process that restores the integrity and function of the skin and the underlying tissue. Such wounds may be the result of a scrape, abrasion, cut, graze, incision, tear, or bruise to the skin. If a wound does not heal in 4-12 weeks, it may be considered chronic. In the case of chronic wounds, the wound may be attenuated at one of the stages of healing or fail to progress through the normal stages of healing. A chronic wound may have been present for a brief period of time, such as a month, or it may have been present for several years.

As used herein, the term "wound healing" refers to a regenerative process with the induction of an exact temporal and spatial healing program comprising wound closure and the processes involved in wound closure. The term "wound healing" encompasses but is not limited to the processes of granulation, neovascularization, fibroblast, endothelial and epithelial cell migration, extracellular matrix deposition, re-epithelialization, and remodeling.

The term "wound closure" refers to the healing of a wound wherein sides of the wound are rejoined to form a continuous barrier (e.g., intact skin).

Also disclosed is a method of treating chronic cutaneous wounds. As used herein, the phrase "chronic cutaneous wound" refers to a non-healing wound that includes, but is not limited to, skin ulcers, bed sores, pressure sores, diabetic ulcers and sores, and other skin disorders. The phrase "chronic cutaneous wound", may be used interchangeably with chronic skin wound or non-healing wound and can be any size, shape or depth, and may appear discolored as compared to normal, healthy skin pigment. Chronic cutaneous wound can bleed, swell, seep pus or purulent discharge or other fluid, cause pain or cause movement of the affected area to be difficult or painful. Chronic cutaneous wounds can become infected, producing elevated body temperatures, as well as pus or discharge that is milky, yellow, green, or brown in color, and is odorless or has a pungent odor. If infected, chronic skin wounds may be red, tender, or warm to the touch.

Chronic cutaneous wounds may be caused by diabetes, poor blood supply, low blood oxygen, by conditions where blood flow is decreased due to low blood pressure, or by conditions characterized by occluded, blocked or narrowed blood vessels. A low oxygen supply can be caused by certain blood, heart, and lung diseases, and/or by smoking cigarettes. Chronic cutaneous wounds can also be the result of repeated trauma to the skin, such as swelling or increased pressure in the tissues, or constant pressure on the wound area. Chronic cutaneous wounds can be caused by a weakened or compromised immune system. A weakened or compromised immune system can be caused by increasing age, radiation, poor nutrition, and/or medications, such as anti-cancer medicines or steroids. Chronic cutaneous wounds can also be cause by bacterial, viral or fungal infections, or the presence of foreign objects.

The inventors of the present disclosure found that in normal skin, the expression of exonic microRNA-198 (miR-198) from the 3'-untranslated region of FSTL1 mRNA is switched to linked open-reading-frame of FSLT1 upon wounding. Furthermore, an inverse correlation was found between the expression pattern of FSTL1, essential for effective migration and miR-198, an inhibitor of keratinocyte migration. Thus, indicating that a post-transcriptional switch controls their context-specific expression and orchestrates wound re-epithelialization.

Further to the finding that shows FSTL1 and miR-198 have a role in wound re-epithelialization, without wishing to be bound by theory, it was believed and demonstrated that the post-transcriptional switch that controls the context-specific expression of FSLT1 and miR-198 is TGF-β signaling. It was demonstrated that TGF-β signaling regulates the switch by down-regulating KH-type slicing regulatory protein essential for miR-198 processing. Thus, the method of promoting wound healing and/or wound closure or the method of treating chronic cutaneous wounds as described herein comprises the administration of a miR-198 inhibitor and/or a follistatin-like-1 (FSTL) polypeptide. In one example, the methods as described herein may comprise the administration of a miR-198 inhibitor. In one example, the methods as described herein may comprise the administration of a follistatin-like-1 (FSTL1) polypeptide. In one example, the methods as described herein may comprise the administration of a miR-198 inhibitor and a follistatin-like-1

(FSTL1) polypeptide. In one example, the miR-198 and/or FSTL1 polypeptide may be provided as a composition. In one example, the miR-198 and/or FSTL1 polypeptide may be provided as a pharmaceutical composition.

In one example, the miR-198 inhibitor and/or FSTL1 polypeptide may be an isolated miR-198 inhibitor and/or an isolated FSTL1 polypeptide. By "isolated," it is meant that the polypeptide is substantially or essentially free from components that normally accompany it in its native environment. An "isolated" peptide, DNA, RNA or miRNA inhibitor does not encompass peptide, DNA, RNA or miRNA inhibitor that are present in a human and/or animal body and does not encompass either natural materials in their native state or natural materials that have been separated into components (e.g., in an acrylamide gel) but not obtained either as pure substances or as solutions.

The term "miRNA", as used herein, is understood as a single stranded non-coding RNA sequence which is capable of interacting with the 3'-untranslated region of a mRNA thus preventing its translation. The terms "microRNA" or "miRNA" that may be used interchangeably herein, are endogenous RNAs, some of which are known to regulate the expression of protein-coding genes at the posttranscriptional level. As used herein, the term "microRNA" refers to any type of micro-interfering RNA, including but not limited to, endogenous microRNA and artificial microRNA. Typically, endogenous microRNA are small RNAs encoded in the genome which are capable of modulating the productive utilization of mRNA. A mature miRNA is a single-stranded RNA molecule of about 21-23 nucleotides in length which is complementary to a target sequence, and hybridizes to the target RNA sequence to inhibit its translation. miRNAs themselves are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to down-regulate gene expression.

In one example, the method as described herein further comprises the administration of TGF-β1 either simultaneously or before or after administration of the composition comprising miR-198 inhibitor and/or the FSTL1 polypeptide. In one example, miR-198 inhibitor and FSTL1 polypeptide may be administered simultaneously or separately from each other.

An "miR-198 inhibitor" refers to any molecule (e.g. non-selective or selective) which inactivates and/or downregulates the activity of miR-198. The inhibitor can be a small molecule, an antisense nucleic acid, a small interfering RNA or a microRNA-based compound. The miR-198 inhibitor may be a direct inhibitor such that it interacts with the miR-198 or with a nucleic acid encoding the miR-198. Alternatively, the miR-198 inhibitor may be an indirect inhibitor which interacts upstream or downstream of the miR-198 in the regulatory pathway and which does not interact with the miR-198 or with a nucleic acid encoding the miR-198. In one example, the miR-198 inhibitor may be an anti-miR-198, peptide nucleic acid (PNA) derivatives of miR-198 inhibitor sequence or Tiny locked nucleic acid (LNA) anti-miRs for seed-sequence of the inhibitor.

The term "peptide nucleic acid (PNA)" as used herein refers to DNA mimics with a pseudopeptide backbone. In one example, the PNA as used herein may be able to form very stable duplex structures with the miR-198, thus competitively inhibit miR-198 functions in cells.

The term "tiny LNA anti-miRs" as used herein refers inaccessible RNA, is a modified RNA nucleotide. In one example, transfection of tiny LNAs into cells resulted in simultaneous inhibition of miRNAs (for example, miR-198) within families sharing the same seed with concomitant upregulation of direct targets. In one example, transfection of tiny LNAs systemically showed long term miRNA silencing.

In one example, the miR-198 inhibitor may have the sequence: 5'-GAACCUAUCUCCCCUCUGGACC-3'(SEQ ID NO: 1), GAACCTATCTCCCCTCTGGACC (SEQ ID NO: 9) or GAACCUAUCUCCCCUCUGGACC (SEQ ID NO: 10). In one example, the miR-198 inhibitor may have 80% or more, 85% or more, 90% or more, 95% or more or 99% or more identity with sequence SEQ ID NO: 1, SEQ ID NO: 9 or SEQ ID NO: 10.

In another example, the miR-198 inhibitor may be either unmodified or modified. In one example, the miR-198 inhibitor may be modified with at least one, at least two, at least three, or all of the following modification/s, such as 1) full or partial 2'-O-methoxy ethyl modification, 2) full or partial phosphorothioate modification, 3) Cholesterol modification of 3' end of the miR-198 inhibitor, 4) full or partial locked nucleic acid modification (LNA) of nucleotides.

In one example, the miR-198 inhibitor may increase or lead to the overexpression of proteins that are typically downregulated by miR-198. In one example, proteins that are downregulated by miR-198 include, but not limited to, urokinase-type plasminogen activator (PLAU), a serine protease involved in degradation of extracellular matrix components, diaphanous homolog 1 (DIAPH1), involved in actin polymerization and laminin gamma 2 chain (LAMC2), an essential component of the basement membrane protein laminin 5. In one example, the method of healing wound may comprise the administration of any one of the proteins selected from the group consisting of urokinase-type plasminogen activator (PLAU), diaphanous homolog 1 (DIAPH1), and laminin gamma 2 chain (LAMC2).

In one example, the FSTL1 polypeptide may have the sequence SEQ ID NO: 2. In one example, the FSTL1 polypeptide may have 80% or more, 85% or more, 90% or more, 95% or more or 99% or more identity with sequence SEQ ID NO: 2. In one example, SEQ ID NO: 2 is as follows:

```
MWKRWLALAL  ALVAVAWVRA  EEELRSKSKI  CANVFCGAGR  ECAVTEKGEP  TCLCIEQCKP   60

HKRPVCGSNG  KTYLNHCELH  RDACLTGSKI  QVDYDGHCKE  KKSVSPSASP  VVCYQSNRDE  120

LRRRIIQWLE  AEIIPDGWFS  KGSNYSEILD  KYFKNFDNGD  SRLDSSEFLK  FVEQNETAIN  180

ITTYPDQENN  KLLRGLCVDA  LIELSDENAD  WKLSFQEFLK  CLNPSFNPPE  KKCALEDETY  240

ADGAETEVDC  NRCVCACGNW  VCTAMTCDGK  NQKGAQTQTE  EEMTRYVQEL  QKHQETAEKT  300

KRVSTKEI
```

In one example, the miR-198 may have 80% or more, 85% or more, 90% or more, 95% or more or 99% or more identity with any one of sequence SEQ ID NOs: 3, 4, 5 or 6. In one example, the miR-198 may be either unmodified or modified.

In one example, SEQ ID NO: 3, which encodes for precursor miR-198 DNA sequence is as follows: 5' TCATTGGTCCAGAGGGGAGATAGGTTCCTGTGATTTTTCCTTCTTCTCTA TAGAATAAATGA 3'.

In one example, SEQ ID NO: 4, which encodes for precursor miR-198 RNA sequence is as follows: 5' UCAUUGGUCCAGAGGGGAGAUAGGUUCCUGUGAUUUUUCCUUCUUCUCUA UAGAAUAAAUGA 3'.

In one example, SEQ ID NO: 5, which encodes for one example of mature miR-198 DNA sequence is as follows: 5' GGTCCAGAGGGGAGATAGGT TC 3'.

In one example, SEQ ID NO: 6, which encodes for one example of mature miR-198 DNA sequence is as follows: 5' GGUCCAGAGGGGAGAUAGGUUC 3'.

In one example, the miR-198 inhibitor may have 80% or more, 85% or more, 90% or more, 95% or more or 99% or more identity with any one of sequence SEQ ID NOs: 7, 8, 9, or 10.

In one example, SEQ ID NO: 7, which encodes for precursor antimiR-198 DNA sequence is as follows: 5' TCATTTATTCTATAGAGAAGAAGGAAAAATCACAGGAACCTATCTCCCCTCTGGACCAATGA 3'.

In one example, SEQ ID NO: 8, which encodes for precursor antimiR-198 RNA sequence is as follows: 5' UCAUUUAUUCUAUAGAGAAGAAGGAAAAAUCACAGGAACCUAUCUCCCCU CUGGACCAAUGA 3'.

In one example, SEQ ID NO: 9, which encodes for one example of mature antimiR-198 DNA sequence is as follows: 5' GAACCTATCTCCCCTCTGGACC 3'.

In one example, SEQ ID NO: 10, which encodes for one example of mature antimiR-198 DNA sequence is as follows: 5' GAACCUAUCUCCCCUCUGGACC 3'.

Also disclosed is a use of miR-198 inhibitor and/or FSTL1 polypeptide in the manufacture of a medicament for treating non-healing wounds or chronic cutaneous wounds. In one example, there is provided a use of miR-198 inhibitor and/or FSTL1 polypeptide in the manufacture of a medicament for promoting wound healing or wound closure. In one example, the medicament further comprises TGF-β1. In one example, the chronic cutaneous wounds are the wounds of a patient suffering or suspected to be suffering from diabetes mellitus. As used herein, the term "diabetes" refers to any of several metabolic conditions characterized by the excessive excretion of urine and persistent thirst. The excess of urine can be caused by a deficiency of antidiuretic hormone, as in diabetes insipidus, or it can be the polyuria resulting from the hyperglycemia that occurs in diabetes mellitus.

As used herein, the phrase "type 1 diabetes mellitus" refers to the first of the two major types of diabetes mellitus, characterized by abrupt onset of symptoms (often in early adolescence), insulinopenia, and dependence on exogenous insulin. It results from a lack of insulin production by the pancreatic beta cells. With inadequate control, hyperglycemia, protein wasting, and ketone body production occur. The hyperglycemia leads to overflow glycosuria, osmotic diuresis, hyperosmolarity, dehydration, and diabetic ketoacidosis, which can progress to nausea and vomiting, stupor, and potentially fatal hyperosmolar coma. The associated angiopathy of blood vessels (particularly microangiopathy) affects the retinas, kidneys, and arteriolar basement membranes. Polyuria, polydipsia, polyphagia, weight loss, paresthesias, blurred vision, and irritability can also occur.

As used herein, the phrase "type 2 diabetes mellitus" refers to the second of the two major types of diabetes mellitus, peaking in onset between 50 and 60 years of age, characterized by gradual onset with few symptoms of metabolic disturbance (glycosuria and its consequences) and control by diet, with or without oral hypoglycemics but without exogenous insulin required. Basal insulin secretion is maintained at normal or reduced levels, but insulin release in response to a glucose load is delayed or reduced. Defective glucose receptors on the pancreatic beta cells may be involved. It is often accompanied by disease of blood vessels, particularly the large ones, leading to premature atherosclerosis with myocardial infarction or stroke syndrome.

In one example, the chronic cutaneous wound is diabetic ulcer. As used herein, the term "ulcer" refers to a local defect or excavation of the surface of an organ or tissue, produced by sloughing of necrotic tissue.

Also disclosed is a pharmaceutical composition comprising a) a miR-198 inhibitor and TGF-β1; or b) the miR-198 inhibitor and a FSTL1 polypeptide; or c) the FSTL polypeptide and TGF-β1; or d) the miR-198 inhibitor and TGF-1 and the FSTL1 polypeptide.

The compositions as described herein may be administered in a number of ways depending upon whether local or systemic treatment is desired and upon the area to be treated. Administration may be topical, pulmonary (e.g., by inhalation or insufflation of powders or aerosols, including by nebulizer, intratracheal, intranasal, epidermal and transdermal) or systemic such as oral, and/or parenteral. In one example, the compositions as described herein may be administered via systemic or topical administration.

Parenteral administration includes intravenous, intraarterial, subcutaneous, intraperitoneal or intramuscular injection or infusion; or intracranial, e.g., intrathecal or intraventricular, administration.

In one example, the administration is via topical administration. Compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

In one example, the composition for topical administration comprises the composition as described herein and a dermatologically acceptable vehicle. The vehicle may be aqueous or nonaqueous. The dermatologically acceptable vehicle used in the topical composition may be in the form of a lotion, a gel, an ointment, a liquid, a cream, or an emulsion. If the vehicle is an emulsion, the emulsion may have a continuous aqueous phase and a discontinuous nonaqueous or oil phase (oil-in-water emulsion), or a continuous nonaqueous or oil phase and a discontinuous aqueous phase (water-in-oil emulsion).

In one example, the composition as described herein may be topically administered using a transdermal patch. In one example, the transdermal patch comprises an adhesive layer for adhering the patch to the skin, and a drug-impermeable backing layer. In one example, the adhesive layer contains the composition as described herein in combination with an adhesive polymer. In this type of system, the composition as described herein is released from the adhesive layer and passes directly to the skin.

In one example, the transdermal system has a reservoir layer containing the composition as described herein. The drug reservoir layer is a liquid, gel, or semisolid compartment containing a drug solution or suspension, where the reservoir layer is positioned in between the adhesive layer and the backing layer. In this type of system, the composition as described herein is released from the reservoir layer and passes through the adhesive layer.

The pharmaceutical excipients used in the topical preparation of the present disclosure may be selected from the group consisting of solvents, emollients and/or emulsifiers, oil bases, preservatives, antioxidants, tonicity adjusters, penetration enhancers and solubilizers, chelating agents, buffering agents, surfactants, one or more polymers, and combinations thereof.

Suitable solvents for an aqueous or hydrophilic topical formulation include water, ethyl alcohol; isopropyl alcohol; mixtures of water and ethyl and/or isopropyl alcohols; glycerin; ethylene, propylene or butylene glycols; DMSO; and mixtures thereof. Suitable solvents for a hydrophobic topical formulation include mineral oils, vegetable oils, and silicone oils. If desired, the composition as described herein may be dissolved or dispersed in a hydrophobic oil phase, and the oil phase may then be emulsified in an aqueous phase comprising water, alone or in combination with lower alcohols, glycerin, and/or glycols.

Suitable emollients include hydrocarbon oils and waxes such as mineral oil, petrolatum, paraffin, ceresin, ozokerite, microcrystalline wax, polyethylene, squalene, perhydrosqualene, silicone oils, triglyceride esters, acetoglyceride esters, such as acetylated monoglycerides; ethoxylated glycerides, such as ethoxylated glyceryl monostearate; alkyl esters of fatty acids or dicarboxylic acids.

Suitable silicone oils for use as emollients include dimethyl polysiloxanes, methyl(phenyl) polysiloxanes, and water-soluble and alcohol-soluble silicone glycol copolymers. Suitable triglyceride esters for use as emollients include vegetable and animal fats and oils including castor oil, safflower oil, cotton seed oil, corn oil, olive oil, cod liver oil, almond oil, avocado oil, palm oil, sesame oil, and soybean oil.

Suitable esters of carboxylic acids or diacids for use as emollients include methyl, isopropyl, and butyl esters of fatty acids. Specific examples of alkyl esters including hexyl laurate, isohexyl laurate, iso-hexyl palmitate, isopropyl palmitate, decyl oleate, isodecyl oleate, hexadecyl stearate, decyl stearate, isopropyl isostearate, dilauryl lactate, myristyl lactate, and cetyl lactate; and alkenyl esters of fatty acids such as oleyl myristate, oleyl stearate, and oleyl oleate. Specific examples of alkyl esters of diacids include diisopropyl adipate, diisohexyl adipate, bis(hexyldecyl) adipate, and diisopropyl sebacate.

Other suitable classes of emollients or emulsifiers which may be used in the topical formulations include fatty acids, fatty alcohols, fatty alcohol ethers, ethoxylated fatty alcohols, fatty acid esters of ethoxylated fatty alcohols, and waxes.

Specific examples of fatty acids for use as emollients include pelargonic, lauric, myristic, palmitic, stearic, isostearic, hydroxystearic, oleic, linoleic, ricinoleic, arachidic, behenic, and erucic acids. Specific examples of fatty alcohols for use as emollients include lauryl, myristyl, cetyl, hexadecyl, stearyl, isostearyl, hydroxystearyl, oleyl, ricinoleyl, behenyl, and erucyl alcohols, as well as 2-octyl dodecanol.

Specific examples of waxes suitable for use as emollients include lanolin and derivatives thereof including lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semisolid lanolin. Also usable as waxes include hydrocarbon waxes, ester waxes, and amide waxes. Useful waxes include wax esters such as beeswax, spermaceti, myristyl myristate and stearyl stearate; beeswax derivatives, e.g., polyoxyethylene sorbitol beeswax; and vegetable waxes including carnauba and candelilla waxes.

Polyhydric alcohols and polyether derivatives may be used as solvents and/or surfactants in the topical formulations. Suitable polyhydric alcohols and polyethers include propylene glycol, dipropylene glycol, polypropylene glycols 2000 and 4000, poly(oxyethylene-co-oxypropylene) glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol, 2-methyl-2,4-pentanediol, 1,3-butylene glycol, 1,2,6-hexanetriol, 2-ethyl-1,3-hexanediol, vicinal glycols having 15 to 18 carbon atoms, and polyoxypropylene derivatives of trimethylolpropane.

Polydydric alcohol esters may be used as emulsifiers or emollients. Suitable polydydric alcohol esters include ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Suitable emulsifiers for use in topical formulations include anonic, cationic, nonionic, and zwitterionic surfactants. Preferred ionic emulsifiers include phospholipids, such as lecithin and derivatives.

Lecithin and other phospholipids may be used to prepare liposomes containing the composition as described herein. Formation of lipid vesicles occurs when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes. Continued high-shear sonication tends to form smaller unilamellar liposomes. Hydrophobic chemicals can be dissolved into the phospholipid bilayer membrane. The lipid bilayers of the liposomes deliver the composition as described herein to keratinocytes by fusing with the cell membrane of the keratinocytes.

In one example, the topical formulation may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting formulation contains micelles, i.e., spherical oil droplets surrounded by a membrane of polar surfactant molecules, dispersed in the aqueous solvent.

Sterols including, for example, cholesterol and cholesterol fatty acid esters; amides such as fatty acid amides, ethoxylated fatty acid amides, and fatty acid alkanolamides may also be used as emollients and/or penetration enhancers.

Suitable viscosity enhancers or thickeners which may be used to prepare a viscous gel or cream with an aqueous base include sodium polyacrylate, xanthan gum, polyvinyl pyrollidone, acrylic acid polymer, carrageenans, hydroxyethyl cellulose, hydroxypropyl cellulose, methyl cellulose, ethyl cellulose, propyl cellulose, hydroxypropyl methyl cellulose, polyethoxylated polyacrylamides, polyethoxylated acrylates, and polyethoxylated alkane thiols.

Suitable preservatives and/or antioxidants for use in topical formulations include benzalkonium chloride, benzyl alcohol, phenol, urea, parabens, butylated hydroxytoluene (BHT), butylated hydroxyanisole (BHA), Tocopherol, and mixtures thereof.

Suitable chelating agents for use in topical formulations include ethylene diamine tetraacetic acid, alkali metal salts thereof alkaline earth metal salts thereof, ammonium salts thereof, and tetraalkyl ammonium salts thereof.

The carrier preferably has a pH of between about 4.0 and 10.0, more preferably between about 6.8 and about 7.8. The pH may be controlled using buffer solutions or other pH modifying agents. Suitable pH modifying agents include phosphoric acid and/or phosphate salts, citric acid and/or citrate salts, hydroxide salts (i.e., calcium hydroxide, sodium hydroxide, potassium hydroxide) and amines, such as triethanolamine. Suitable buffer solutions include a buffer comprising a solution of monopotassium phosphate and dipotassium phosphate, maintaining a pH of between 5.8 and 8; and a buffer comprising a solution of monosodium phosphate and disodium phosphate, maintaining a pH of between 6 and 7.5. Other buffers include citric acid/sodium citrate, and dibasic sodium phosphate/citric acid.

The various examples of creams, ointments, lotions, solutions, gels, sprays and patches may incorporate the composition as described herein as the active ingredient, in combination with penetration enhancing agents and other active agents acting synergistically on the skin for the promotion of wound healing or wound closure or the treatment of chronic cutaneous wound.

In one example, of the topical formulation include miR-198 inhibitor and/or FSTL1 polypeptide and/or TGF-β1 in a concentration of from about 0.005% by weight to about 50% by weight. Formulations containing miR-198 inhibitor and/or FSTL1 polypeptide and/or TGF-β1 in an aqueous carrier typically contain from about 0.005% by weight to about 0.5% by weight miR-198 inhibitor and/or FSTL1 polypeptide and/or TGF-β1, preferably about 0.01% by weight to about 0.1% by weight, more preferably about 0.01% by weight to about 0.05% by weight. Formulations containing miR-198 inhibitor and/or FSTL1 polypeptide and/or TGF-β1 in an oil or wax carrier typically contain from about 0.005% to about 50% by weight of miR-198 inhibitor and/or FSTL1 polypeptide and/or TGF-β1, preferably about 0.01% by weight to about 25% by weight, more preferably about 0.1% by weight to about 10% by weight, most preferably from about 0.1% by weight to about 5% by weight. Creams, lotions, or other emulsions containing an oil phase and an aqueous phase typically contain miR-198 inhibitor and/or FSTL1 polypeptide and/or TGF-β1 in an amount of from about 0.005% to about 25% by weight, preferably about 0.005% to about 10% by weight, more preferably about 0.01% to about 5% by weight. The creams, lotions, or other emulsions may be prepared as water-in-oil or oil-in-water emulsions; in either case, the hydrophobic compound miR-198 inhibitor and/or FSTL1 polypeptide and/or TGF-β1 is dissolved or dispersed in the oil phase.

A suitable formulation comprises miR-198 inhibitor and/or FSTL1 polypeptide and/or TGF-β1 in a concentration of from about 0.1 to about 0.3 mg/mL (0.01% to 0.03%), and the preservative benzalkonium chloride in a concentration of from about 0.05 to about 0.2 mg/mL. The formulation is provided in a vehicle comprising water having a pH of between about 6.8 and about 7.8 as a solvent. The formulation further comprises sodium chloride, a dibasic sodium phosphate/citric acid buffer, and optionally sodium hydroxide and/or hydrochloric acid to adjust the pH.

The topical formulation may be provided to a patient having an open wound, wound or chronic cutaneous wound in a bottle designed to administer the formulation in a dropwise fashion. The patient may then administer the topical formulation at regular intervals to affected tissue, in an amount of from 1 drop per 5 square centimeters of affected skin to 5 drops per square centimeter of affected skin, preferably 1 drop (where 1 drop is about 0.02 mL to about 0.05 mL, more preferably about 0.03 mL) per 5 square centimeters of affected skin to 1 drop per square centimeter of affected skin, more preferably 1 drop per 2 square centimeters of affected skin. In various embodiments, topical formulations may be administered at intervals ranging from four times per day to once per week, preferably two times per day to twice a week, more preferably two times per day to once a day. Frequency of administration may be adjusted depending on concentration of in the topical formulation, i.e., a topical formulation having a high concentration of the composition as described herein may be administered less frequently than a similar formulation having a lower concentration.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Compositions as described herein include, but are not limited to, solutions, emulsions, and liposome-containing formulations. These composition may be generated from a variety of components that include, but are not limited to, preformed liquids, self-emulsifying solids and self-emulsifying semisolids.

The formulations as described herein, which may conveniently be presented in unit dosage form, may be prepared according to conventional techniques well known in the pharmaceutical industry. Such techniques, include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions as described herein may be formulated into any of many possible dosage forms such as, but not limited to, tablets, capsules, liquid syrups, soft gels, suppositories, and enemas. The compositions as described herein may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one example, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions as described herein may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

The term "therapeutically effective amount" as used herein includes within its meaning a sufficient but non-toxic amount of the miR-198 inhibitor and/or follistatin-like-1 (FSTL1) polypeptide and/or TGF-β1 to provide the desired therapeutic effect. The exact amount required will vary from subject to subject depending on factors such as the species being treated, the age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of the composition, and can generally be estimated based on EC50s found to be effective in in vitro and in vivo animal models or based on the examples described herein. In general, dosage is from 0.01 μg to 100 g/kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the composition is administered in maintenance doses, ranging from 0.01 μg to 100 g/kg of body weight, once or more daily, to once every 2 years.

In one example, the composition comprising miR-198 inhibitor and/or FSTL1 polypeptide as described herein may be administered in an amount of between any one of about 0.01 μg, 0.05 μg, 0.1 μg, 0.5 μg, 1 μg, 5 μg, 10 μg, 20 μg, 30 μg, 40 μg, 50 μg, 60 μg, 70 μg, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 500 μg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg to any one of about 0.01 μg, 0.05 μg, 0.1 μg, 0.5 μg, 1 μg, 5 μg, 10 μg, 20 μg, 30 μg, 40 μg, 50 μg, g 60 g, 70 g, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 500 μg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg, 300 mg/kg body weight.

In one example, the miR-198 inhibitor and FSTL1 polypeptide may be administered independently or as a combination of each other. In one example, miR-198 inhibitor and FSTL1 polypeptide may be administered independently of each other in an amount of between any one of about 0.01 μg, 0.05 μg, 0.1 μg, 0.5 μg, 1 μg, 5 μg, 10 μg, 20 μg, 30 g, 40 μg, 50 μg, 60 μg, 70 μg, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 500 pig, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg to any one of about 0.01 μg, 0.05 μg, 0.1 μg, 0.5 μg, 1 μg, 5 μg, 10 μg, 20 μg, 30 μg, 40 μg, 50 μg, 60 μg, 70 μg, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 500 μg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg, 300 mg/kg body weight. In one example, miR-198 inhibitor and FSTL1 polypeptide may be administered independently of each other in an amount of between about 10 μg to 300 mg/kg body weight.

In one example, the TGF-β1 may be administered in an amount of between any one of about 0.01 μg, 0.05 μg, 0.1 μg, 0.5 μg, 1 μg, 5 μg, 10 μg, 20 μg, 30 μg, 40 μg, 50 μg, 60 μg, 70 μg, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 500 μg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg to any one of about 0.01 μg, 0.05 μg, 0.1 μg, 0.5 μg, 1 μg, 5 μg, 10 μg, 20 μg, 30 μg, 40 μg, 50 μg, 60 μg, 70 μg, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 500 μg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg, 300 mg/kg body weight. In one example, the TGF-β1 may be administered in an amount of between 10 μg to 300 mg/kg body weight.

As used herein, the term "about", in the context of amounts or concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Also disclosed is a method of identifying chronic cutaneous wound in a sample, wherein the method comprises: analyzing expression level of miR-198. The method of identifying chronic cutaneous wound as described herein may further comprise analyzing expression of FSTL1 gene and/or FSTL1 polypeptide.

Figure 11B:
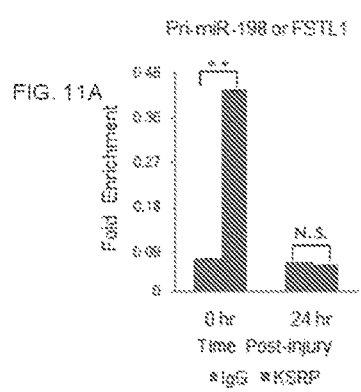
FIG. 11 a) shows RNA immunoprecipitations on epidermal lysates from explants, 0 hour or 24 hours after injury using anti-KSRP antibody or IgG control. Quantitative RT-PCR representing fold enrichment of transcripts reveals specific binding of KSRP to FSTL1 transcript only at 0 hours but not 24 hours after injury (n=3). **P<0.001. Student's t-test was used to calculate P value and error bars denote mean±s.e.m. b) Wild type and mutant Pre-miR-198 sequences used in RNA gel retardation assay (SEQ ID NOs: 3, 70 and 71). Mature miR-198 sequence is marked in red, terminal loop sequence shown in green, whereas the mutated sequences are shown in blue within boxes. Thus.

In one example, the expression or an increased expression of miR-198 may indicate that the wound is a non-healing wound or a chronic cutaneous wound. In one example, the increased expression of miR-198 may be determined relative to a control expression level obtained from one or more wounds which are not chronic cutaneous wound or are not non-healing wound. In one example, the expression of miR-198 may be assayed using sequences as used in FIG. 11.

In one example, the reduced or non-expression of FSTL1 gene and/or reduced level or absence of FSTL1 polypeptide indicates that the wound is a chronic cutaneous wound or a non-healing wound. In one example, the reduced expression of FSTL1 or reduced presence of FSTL1 polypeptide is determined relative to a control expression or polypeptide level obtained from a sample from one or more wounds which are not chronic cutaneous wound or are not non-healing wound.

The term "relative" when used with reference to the amount of a miR-198 and/or FSTL1 gene and/or FSTL1 polypeptide relates to the amount of a first miR-198 and/or FSTL1 gene and/or FSTL1 polypeptide obtained from a non-chronic cutaneous wound or obtained from a non-diabetic subject, compared to the amount of a second miR-198 and/or FSTL1 gene and/or FSTL1 polypeptide obtained from a subject suspected of having chronic cutaneous wound or obtained from a diabetic subject or a subject suspected of having diabetes.

The term "increased" as used herein refers to greater amount, intensity, or degree relative to a control expression level. The increased in expression may be at least about 5%, 10%, 15%, 20%, 25%, 30%, 35%, 40%, 45%, 50%, 55%, 60%, 65%, 70%, 75%, 80%, 85%, 900/%, 95% or 100% more than that of a control expression level.

The term "reduced" as used herein refers to decreased amount, intensity, or degree relative to a control expression level. The reduced in expression may be at least about 5%, 10%, 15%, 20%, 25%, 30%, 35%, 40%, 45%, 50%, 55%, 60%, 65%, 70%, 75%, 80%, 85%, 90%, 95% or 100% less than that of a control expression level.

In one example, the method of identifying chronic cutaneous wound may include analyzing the expression of protein that is negatively regulated by miR-198 such as, but not limited to, urokinase-type plasminogen activator (PLAU), a serine protease involved in degradation of extracellular matrix components, diaphanous homolog 1 (DIAPH1), involved in actin polymerization and laminin gamma 2 chain (LAMC2), an essential component of the basement membrane protein laminin 5. As exemplified in FIGS. 3B, 8 and 9, knockdown of DIAPH1, PLAU and LMAC2 using gene-specific siRNA significantly suppressed wound healing and/or closure. Thus, as exemplified in FIG. 3D, chronic cutaneous wound or a non-healing wound has decreased or absent DIAPH1, PLAU and LAMC2 expression.

In one example, the expression of miR-198 FSTL1 gene and FSTL1 polypeptide may be measured in a sample. In one example, the sample may include any cells found at the wound edge. In one example, the expression of miR-198, FSTL1 gene and FSTL1 protein may be measured in keratinocytes in the epidermis at the wound edge. As used herein, the term "epidermis" refers to the outermost layers of cells in the skin. The epidermis is a stratified squamous epithelium, comprises of proliferating basal and differentiated suprabasal keratinocytes. Keratinocytes are the most common type of skin cells found at the epidermis layer of skin.

Also disclosed is the use of miR-198, FSTL1 gene and/or FSTL1 polypeptide as a biomarker for identifying a chronic cutaneous wound. In one example, the use of miR-198 and FSTL1 polypeptide as a biomarker for identifying a chronic cutaneous wound is illustrated by the Experimental Section below, in particular FIG. 10.

The present disclosure also contemplates a variety of kits for use in the disclosed methods. In one example, a kit for promoting wound healing or wound closure may comprise: i) a miR-198 inhibitor and/or ii) a follistatin-like-1 (FSTL1) polypeptide; and iii) instructions to administer the miR-198 inhibitors simultaneously or separately from administration of the FSTL1. In one example, the kits may further comprise iv) TGF-β1 and (v) instructions to administer the TGF-β1 simultaneously or separately from administration of miR-198 inhibitor and/or a follistatin-like-1 (FSTL1) polypeptide.

The instructions may be provided in paper form or in computer-readable form, such as a disc, CD, DVD or the like. The kits may optionally include quality control reagents, such as sensitivity panels, calibrators, and positive controls.

In one example, a kit for identifying a chronic cutaneous wound may comprise reagents to analyse expression level of miR-198 and/or analyse expression level of FSTL1 gene and/or FSTL1 polypeptide level and an instruction to determine the relative expression of miR-198 and/or FSTL1 gene and/or FSTL1 polypeptide indicates that a wound is a chronic cutaneous wound. In one example, the kit may comprise the reagents used in the Experimental Section below, in particular experiments related to FIGS. 3, 10 and 11.

In one example, the expression or an increased expression of miR-198 may indicate that the wound is a non-healing wound or a chronic cutaneous wound. In one example, the increased expression of miR-198 may be determined relative to a control expression level obtained from one or more wounds which are not chronic cutaneous wound or are not non-healing wound. In one example, the expression of miR-198 may be assayed using sequences as used in FIG. 11.

In one example, the reduced or non-expression of FSTL1 gene and/or reduced level or absence of FSTL1 polypeptide indicates that the wound is a non-healing wound. In one example, the reduced expression of FSTL1 or reduced presence of FSTL1 polypeptide is determined relative to a control expression or polypeptide level obtained from one or more wounds which are chronic cutaneous wound or are not non-healing wound.

The kits can further incorporate a detectable label, such as a fluorophore, radioactive moiety, enzyme, biotin/avidin label, chromophore, chemiluminescent label, or the like, or the kits may include reagents for labeling the nucleic acid primers, the nucleic acid probes or the nucleic acid primers and nucleic acid probes for detecting the presence or absence of at least one mutation as described herein. The primers and/or probes, calibrators and/or controls can be provided in separate containers or pre-dispensed into an appropriate assay format, for example, into microtiter plates.

The kits can optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), may also be included in the kit. The kit may additionally include one or more other controls. One or more of the components of the kit may be lyophilized and the kit may further comprise reagents suitable for the reconstitution of the lyophilized components.

The various components of the kit optionally. are provided in suitable containers. As indicated above, one or more of the containers may be a microtiter plate. The kit further can include containers for holding or storing a sample (e.g., a container or cartridge for a blood or urine sample). Where appropriate, the kit may also optionally contain reaction vessels, mixing vessels and other components that facilitate the preparation of reagents or the test sample. The kit may also include one or more instruments for assisting with obtaining a test sample, such as a syringe, pipette, forceps, measured spoon, or the like.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Materials and Methods

Human Skin and Ex Vivo Organ Culture and Injury Assay

Ex vivo injury assays were carried out using a human skin organ culture model system as described in I. Pastar et al., Mol. Med., 16, 92, March, 2010. At the time points indicated after wounding, tissue samples were processed for histology or RNA analysis. For immunohistochemistry, tissue samples were fixed in 10% neutral buffered formalin for 48 hours before dehydration and embedding in paraffin blocks. Tissue for RNA extraction was snap-frozen in liquid nitrogen and stored at −80° C. until RNA isolation. Skin biopsies were excised from the margins of non-healing ulcers of diabetic patients, prior to scheduled amputations. Samples were processed as above for immunohistochemistry. Chronic diabetic ulcer wound biopsy samples were collected from 5 patients between the age group of 45-55 years. This study was approved by the local domain specific ethical review board in accordance with the Declaration of Helsinki and all participants gave written, informed consent.

Cell Culture

N/TERT-1 keratinocytes derived from normal human epidermal keratinocytes (HEKs) and immortalized with the telomerase catalytic subunit were used for experiments. Cells were cultured in K-SFM (Life Technologies) supplemented with 0.2 ng/ml of epidermal growth factor (EGF), 25 μg/ml of bovine pituitary extract, 0.4 mM $CaCl_2$ and penicillin/streptomycin. Cell cultures were maintained at low confluence to prevent differentiation and passaged before they reached 40% confluence. Lenti-X 293T cells (Clonetech) were cultured in DMEM with 10% fetal calf serum containing penicillin/streptomycin.

Antibodies

Antibodies used in this study are as follows. Goat anti-FSTL1 antibody (#ab11805, Abcam), Rabbit anti-DIAPH1 antibody (#5486, Cell Signaling), Mouse anti-LAMC2 antibody (#sc25341, Santacruz biotechnologies), Rabbit anti-PLAU (#ab24121, Abcam), Mouse anti-TGF-β1 (#NCL-TGFB, Novocastra), Rabbit anti-KSRP antibody (#A302-22A, Bethyl laboratories), Chicken anti-goat Alexa 488 (Molecular probes).

RNA Isolation from Skin

Total RNA from skin samples was isolated by a two-step RNA isolation method. Skin biopsies were homogenized in TRIZOL. Total RNA was extracted using chloroform phase separation and isopropanol precipitation according to TRIZOL manufacturer's instructions (Life Technologies). RNA from precipitate was further subjected to column purification (Exiqon). Isolated RNA was subjected to quality control analysis by Nano-drop (Thermo Scientific) and Bioanalyzer (Agilent Technologies) to assess the concentration and integrity of isolated RNA.

Quantification of microRNA and mRNA

Total RNA (50 ng) was reverse transcribed using miRNA specific primers (Applied Biosystems, Life Technologies, USA) according to TaqMan miRNA Reverse Transcription Kit (Life Technologies, USA). Real time analysis of the miRNA expression was carried out using TaqMan probes. Ct values of miRNAs were normalized against U6 snRNA internal control and values plotted as relative transcript abundance. Total RNA (500 ng) was reverse transcribed with Superscript III (Life Technologies, USA) and anchored oligodT primer as per the manufacturer's instructions. Transcript levels were measured by quantitative RT-PCR using SYBR green PCR master mix (Applied Biosystems, Life Technologies, USA) using gene specific primers listed in Tables 1-3. Ct values were normalized to endogenous ribosomal large subunit P0 (RPLP0) values which have been specifically recommended for use in keratinocytes. For the detection of FSTL1 mRNA by semi quantitative RT PCR, the PCR amplification cycles were limited to 28. All experiments were performed in three biological replicates and representative figures are shown.

Microarray Analysis

N/TERT-1 keratinocytes were transfected with 50 nM of negative control or miR-198 mimics using Dharmafect transfection reagent according to manufacturer's protocol. 48 hours post-transfection, total RNA was isolated using the Exiqon miRcury RNA isolation kit. 250 ng of total RNA was converted into biotinylated cRNA using a TargetAmp Nano-g Biotin-aRNA labeling kit (Epicenter). 750 ng of biotinylated cRNA was hybridized to HT-12 V4 expression bead chip (Illumina) using samples in triplicate. Hybridization, washing and scanning were performed according to the manufacturer's protocol. Data extracted was normalized and analyzed using Illumina BeadStudio.

In Vitro Scratch Wounding Assays

N/TERT-1 keratinocytes were transfected with miRIDIAN miRNA mimics at 50% confluence (Dharmacon). As a control, a non-targeting sequence encoding *Caenorhabditis elegans* miR-239b with no known human targets was used. Cells were transfected with 50 nM of miRNA mimic using Dharmafect 1 according to the manufacturer's protocol. Transfection efficiency was assessed based on co-transfection of SiGloRed transfection indicator. Using an IncuCyte Wound Maker, accessory scratch wounds were made simultaneously in all culture wells 48 hours post-transfection, and scratch area was monitored over 24 hours using IncuCyte Live-Cell Imaging System (Essen BioScience). Scratch wound results were compiled from 6 wells with one scratch in each well. 24 hours was taken as the final time point analysis as this is when closure of the control scratch wound was observed. To knock-down FSTL1, DIAPH1, PLAU and LAMC2, 50 nM of smart-pool siRNA against FSTL1—the ORF sequence (Dharmacon) along with a negative control siRNA were used to transfect keratinoctyes. A non-targeting SiRNA was transfected as negative control. Transfection was performed using Dhramafect 1 transfection reagent.

Inhibition of miR-198/Drosha and Effect on Target Gene Expression

5'fluorescein-labeled, phosphorothioate-modified power inhibitors against mature miR-198 (anti-miR-198), or a negative control inhibitor, were purchased from Exiqon. N/TERT-1 cells were transfected with 50 nM of the inhibitors using Dharmafect 1 transfection reagent. 48 hrs post-transfection, target proteins were subjected to immunocytochemistry using respective antibodies. For the knock-down of Drosha, N/TERT-1 cells were transfected with smart-pool siRNAs against human Drosha and total RNA was isolated at 3 days post transfection.

Proliferation Assays

N/TERT-1 keratinocytes were monitored by image analysis over 48 hours after transfection. Cells were transfected at low density and 24 hours post-transfection, imaging was carried out in subconfluent states using IncuCyte Live-Cell Imaging System (Essen BioScience). Proliferation was calculated by IncuCyte software algorithm to output a proliferation index corresponding to change in confluence of each well. These measurements are an average of 6 wells for each treatment.

Immunohistochemistry

Five micron tissue sections were cut and mounted on polylysine-coated glass slides (Thermo Scientific). Sections were de-paraffinized in xylene and rehydrated using descending ethanol concentrations and finally into phosphate buffered saline (PBS). Endogenous peroxidase was quenched by immersing the slides in 3% hydrogen peroxide in methanol for 30 minutes. If antigen retrieval was needed (dependant on the antibody), this was done in a programmable pressure cooker using "target retrieval solution", pH 6.0 (Dako). Non-specific reactivity in the tissues was blocked by incubation in 10% goat serum in PBS before incubating with the primary antibody at room temperature. Primary antibodies were removed by washing before incubation for with species matched secondary HRP-labeled polymer antibodies (Dako). Chromogen 3,3'-diaminobenzidine (Dako) was used as substrate for colour development. Slides were counterstained with hematoxylin before dehydration and mounting with DPX (Sigma). For non-specific blocking in experiments with goat primary antibodies, 3% BSA in PBS was substituted for 10% goat serum. Images were acquired on a Zeiss Axioimager microscope.

Immunocytochemistry

Keratinocytes cultured on coverslips were fixed using cold acetone methanol. Coverslips were submerged in 5% BSA in PBS to block non-specific adherence, cells were incubated with primary antibodies diluted in 5% BSA for overnight at 4° C. Cells were washed in three changes of PBS with gentle rocking prior to incubation with species matched secondary antibodies conjugated to Alexa probes (Molecular Probes, Invitrogen, USA) for 1 hr at room temperature. Unbound antibodies were removed by washing PBS and nuclei were counterstained with DAPI (100 ng/ml) before a final wash in three changes of PBS with gentle rocking. Cells were mounted using FluorSave mounting media and image acquisition was done in Olympus FluoView FV1000.

miRNA In Situ Hybridization

5μ sections were processed and boiled in pretreatment solution (Panomics), washed in PBS, followed by protease (Panomics) treatment at 37° C. Sections were incubated with LNA probes [5'-DIG labeled LNA probes specific for miR-198 or scrambled probe with no homology to known vertebrate miRNAs (Exiqon)] in hybridization buffer (Roche) at 51° C. for 4 hours. Following stringent wash, sections were blocked with 10% Goat serum and further incubated with anti-DIG alkaline phosphatase (Roche) overnight at 4° C. Sections were washed in PBS-T (0.1%) and miRNA bound LNA probes were detected by Fast red substrate (Panomics). After counterstaining with DAPI, slides were mounted using FluorSave (Merck). Image acquisition was performed with Olympus FluoView FV1000 using TRITC filter.

Luciferase Assay

For generation of chimeric constructs with the target 3'UTR linked to a firefly reporter gene, the 3'UTR fragment spanning miR-198 binding site was amplified from parental 3'UTR clone (Genecopea) using specific primers and subcloned into the multiple cloning site of pmirGLO dual luciferase miRNA target expression vector. FSTL1 3' UTR with and without pre-miR198 stem loop were amplified and subcloned from parental full length construct (Origene). The chimeric constructs were co-transfected with miR-198 or a non-targeting negative control mimic using Effectene (Qiagen) in 293T cells. Firefly and Renilla luciferase activities were measured 48 hrs post transfection using Dual luciferase reporter assay system (Promega). The firefly luminescence was normalized to Renilla luminescence values as an internal control for transfection efficiency. For the mutant 3'UTRs, the miR198 binding site UCUGGAC was converted to UUCAAGU using Quickchange site directed mutagenesis kit (Stratagene) as per manufacturer's instructions.

RNA Immanoprecipitation (RIP)

Keratinocytes treated with 5 ng/ml of TGF-β1 or mock treated, were lysed in RIPA buffer (50 mM Tris-Cl, pH 7.5, 150 mM NaCl, 1% NP40, 0.5% Sodium deoxycholate, 0.025% Sodium dodecyl sulphate, 200 U/ml of RNAseOUT and protease inhibitor cocktail). After clarifying the lysate at 13,000×g for 10 min, the cell extract was incubated with 2 μg of rabbit anti-KSRP antibody (Bethyl laboratories, Texas, USA) or control rabbit IgG, overnight at 4° C. The antigen antibody complex was pulled down with 25 µl (resin volume) of protein A sepharose pre-equilibrated with RIPA buffer at 4° C. for 1 hr. The resin bound to the antigen-antibody complex was washed thrice with RIPA buffer and once with PBS. The immunoprecipitated RNA bound to the resin was extracted using Exiqon miRcury RNA isolation kit. Reverse transcription of the immunoprecipitated RNA as well as the input extract RNA (10%) was carried out with Superscript III (Invitrogen) reverse transcriptase. 4 µl of the cDNA was used in qRT-PCR using primers spanning Pre-198 in FSTL1 mRNA. Results were normalized to input RNA levels and plotted as fold enrichment compared to IgG control RIP. For RIP with skin samples, biopsies were snap frozen immediately in liquid N2 at 0 hr or 24 hr post injury. The epidermis were peeled off from the dermis after dispase treatment overnight and homogenized in RIPA buffer, clarified at 10,000 g for 10 min and processed for RIP as above.

In Vitro Precursor miRNA Processing Assay

For preparation of precursor miR-198, pBSKS constructs containing premiR-198 sequence (obtained from miRBase) under T7 RNA polymerase promoter were linearized and transcribed in the presence of radioactive [32P]-UTP. The run off transcripts were resolved through 8% poly-acrylamide gel, detected by autoradiography and further gel purified in 0.3 M NaCl, overnight at 4° C. The purified premiR-198 was denatured at 90° C. for 2 min and refolded by slow cooling to room temperature in a buffer containing 25 mM Tris-Cl, pH 7.4, 100 mM NaCl, 5 mM $MgCl_2$ and 10% Glycerol. The refolded premiR-198 was stored in aliquots at −20° C. until further use. For the preparation of cytoplasmic extracts as the source of Dicer enzyme, sub confluent 293T cells were lysed in buffer containing 25 mM Tris-Cl, pH 7.4, 150 mM NaCl, 5 mM $MgCl_2$, 0.25% NP-40 and protease inhibitor cocktail (Roche) for 10 min on ice. After clarifying the extract at 10,000 g for 10 min, protein concentration was measured using BCA assay kit (Peirce biotechnology). In vitro precursor miRNA processing assay was carried out with 50 µg of 293T extract and premiR-198 in the presence or absence of recombinant KSRP protein (Origene) for 60 min at room temperature. Samples were processed further with one round of phenol:chloroform extraction and resolved through 8% denaturing poly acrylamide gel electrophoresis. In order to track the position of mature miR-198, the premiR-198 was treated with Shortcut RNase III (New England biolabs) and processed as above. Reaction products were exposed to storage phosphor screens (GE health care) and detected using STORM phosphorimager (GE health care).

Gel Retardation Assay

The pre-miR-198 substrate for gel retardation assay was prepared as described above. Pre-miR-198 transcripts with mutated terminal loop and stem sequences (FIG. 11B) were generated by mutating the parental plasmid (pBSKS) constructs with Quickchange site directed mutagenesis Kit (Stratagene). Recombinant KSRP protein (0.5 µM) was incubated with the wild type or mutant pre-miR-198 transcripts in 20 µl of reaction buffer containing 30 mM Tris HCl, pH 7.4, 5 mM $MgCl_2$, 50 mM KCl, 0.5 mM DTT, 40 u/ml of RNaseOUT, 250 µg/ml of yeast tRNA and 10% glycerol. After 30 min at room temperature, reaction products were resolved through 6% native polyacrylamide gel electrophoresis. Gel was dried and the protein RNA complex and unbound RNA were visualized by phosphorimaging.

Statistical Analysis

Values are reported as the mean±the standard error. Statistical significance between 2 samples was determined with two-tailed Student's t test using GraphPad InStat 3.0 software (GraphPad Software, Inc.).

TABLE 1

List of primers used for RNA quantification

|  | Forward primer | Reverse primer | Remarks |
|---|---|---|---|
| FSTL1 3'-UTR | gagttggccctgtctcttctt SEQ ID NO: 11 | ctttcccactctcttcctgct SEQ ID NO: 12 | Spans the precursor miR198 |
| FSTL1 ORF | aatccaagatctgtgccaatg SEQ ID NO: 13 | gctgtacagacccaatttcca SEQ ID NO: 14 | Binds to Exon 3 and Exon 9 |
| FSTL1 primary transcript | gggatctctgggaatggaata SEQ ID NO: 15 | acactgataggccacaaatgc SEQ ID NO: 16 | Binds within Intron 10 |
| ITGA3 | taaatggctgggctaccctat SEQ ID NO: 17 | gggtccgcttaaagaagtcac SEQ ID NO: 18 |  |
| ISG20 | tgagggagagatcaccgatta SEQ ID NO: 19 | gctcatgtcctctttcagtgc SEQ ID NO: 20 |  |
| IRAK2 | caagtgattctcctgcctcag SEQ ID NO: 21 | tcaagcctgtaatcccaacac SEQ ID NO: 22 |  |
| RSAD2 | gtgcctggatttcatgtcagt SEQ ID NO: 23 | atgcttgctttctctgagctg SEQ ID NO: 24 |  |
| LAMC2 | ctgggttgtgcacatttcttt SEQ ID NO: 25 | aaatacagaagcaaggcagca SEQ ID NO: 26 |  |
| LAMC2 ORF | agtggaaggagagctggaaag SEQ ID NO: 27 | gaccagcccctcttcatctac SEQ ID NO: 28 | Binds within ORF sequence |
| PLAU | gcttgtccaagagtgcatggt SEQ ID NO: 29 | agggctggttctcgatggt SEQ ID NO: 30 |  |

TABLE 1-continued

List of primers used for RNA quantification

| | Forward primer | Reverse primer | Remarks |
|---|---|---|---|
| PLAU ORF | tcactggctttggaaaagaga SEQ ID NO: 31 | gtggtgacttcagagccgtag SEQ ID NO: 32 | Binds within ORF sequence |
| DIAPH1 | aggaagcatgagggcaactat SEQ ID NO: 33 | cccaggaatagtccaaaggag SEQ ID NO: 34 | |
| DIAPH1 ORF | agctgccacagatgaaaaga SEQ ID NO: 35 | tcttggggtcaaagaggaagt SEQ ID NO: 36 | Binds within ORF sequence |
| EDEM1 | tgaaaaggtagggctgagtga SEQ ID NO: 37 | gcagggaagaggcactagaat SEQ ID NO:38 | |
| RPIA | gagcggtatggtatggaatga SEQ ID NO: 39 | gcatttctggtcaactgcttc SEQ ID NO: 40 | |
| MYD88 | gcatgatcttgttgaggcatt SEQ ID NO: 41 | atggcaaatatcggcttttct SEQ ID NO: 42 | |
| ICAM1 | gcactatgcagctccagtttc SEQ ID NO: 43 | caagactgcagtgaaccatga SEQ ID NO: 44 | |
| KRT14 | catgagtgtggaagccgacat SEQ ID NO: 45 | gcctctcagggcattcatctc SEQ ID NO:46 | |
| KHSRP | ctgttttgtttggcgagagag SEQ ID NO: 47 | Gagacacagaacaggcgagag SEQ ID NO: 48 | |
| HuR | ttgtaagtcaccgccagtacc SEQ ID NO: 49 | Tcacatggtcatggtcaaaga SEQ ID NO: 50 | |
| RPLP0 | cagattggctacccaactgtt SEQ ID NO: 51 | Gggaaggtgtaatccgtctcc SEQ ID NO: 52 | |

TABLE 2

List of primers used for amplifying miR198 target 3'UTRs

| | Forward primer | Reverse primer |
|---|---|---|
| DIAPH1 | tcca *gagctc* ctaaggaagcagggagcaaat SEQ ID NO: 53 | tcca *tctaga* gcccacccacttctcttttag SEQ ID NO: 54 |
| LAMC2 | cca *gagctc* gggtgtgagaatgatcaagga SEQ ID NO: 55 | cca *tctaga* cccagctgaagtgtgagtagg SEQ ID NO: 56 |
| PLAU | tcca *gagctc* taggctctgcacagatggatt SEQ ID NO: 57 | tcca *tctaga* gccccaggagtgacctataac SEQ ID NO: 58 |
| KHSRP | tcca *gagctc* aggctcaatgaatcgaatgaa SEQ ID NO: 59 | tcca *tctaga* tacaacacctggtccaaggaa SEQ ID NO: 60 |
| FSTL1 | cca *gagctc* atcccagcatcttctccactt SEQ ID NO: 61 | cca *tctaga* taattggggaaaggaaacc SEQ ID NO: 62 |

Italics represent restriction enzymes used for cloning purpose

TABLE 3

Probe sequences used for in situ hybridization:

| Probe | Probe Sequence | Vendor |
|---|---|---|
| miR-198 | GAACCTATCTCCCCTCTGGACC (SEQ ID NO: 63) | Exiqon |
| FSTL1 | Probeset covers region 2106 to 3714 in mRNA | Panomics |
| Scramble | GTGTAACACGTCTATACGCCCA (SEQ ID NO: 64) | Exiqon |

Results

Figure 5C:
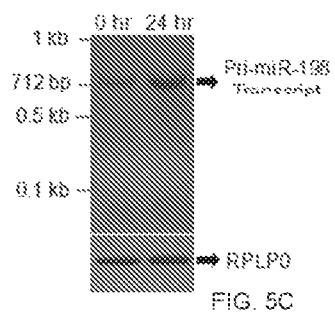
Figure 5D:
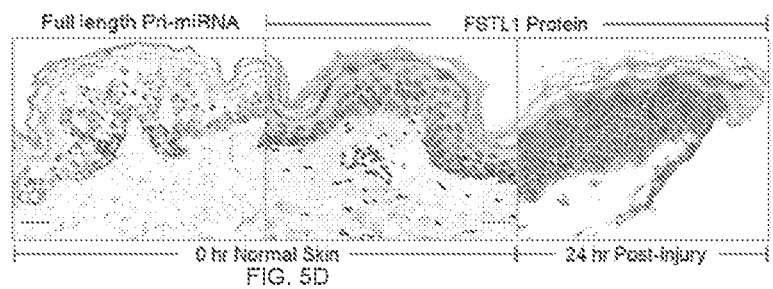
Figure 6A:
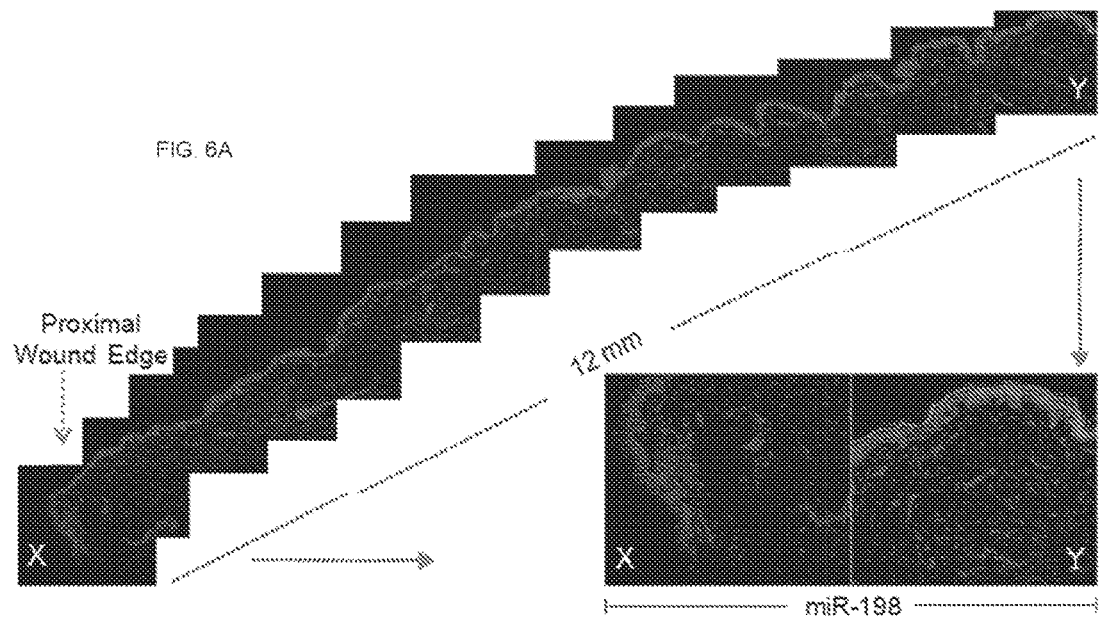
FIG. 6 shows histological images of assays done on skin section after injury. a) shows in situ hybridization for miR-198 in skin section from ex vivo skin biopsy with the inner diameter of 25 mm after 24 hr of injury response. In situ images were acquired contiguously from one wound edge (proximal) to the center of the biopsy (distal) and stitched manually. A gradient of injury response resulting in down-regulation of miR-198 is observed from the proximal wound edge compared to the distal portion of the biopsy (<12 mm). Inset x) magnified images of the proximal wound edge with no detectable miR198 and y) center of the biopsy with miR-198 expression. b) shows immunohistochemistry for FSTL1 protein from the same ex vivo skin biopsy reveals expression at the proximal wound edge. Inset x) and y) magnified images of proximal and distal ends respectively.
Figure 6B:
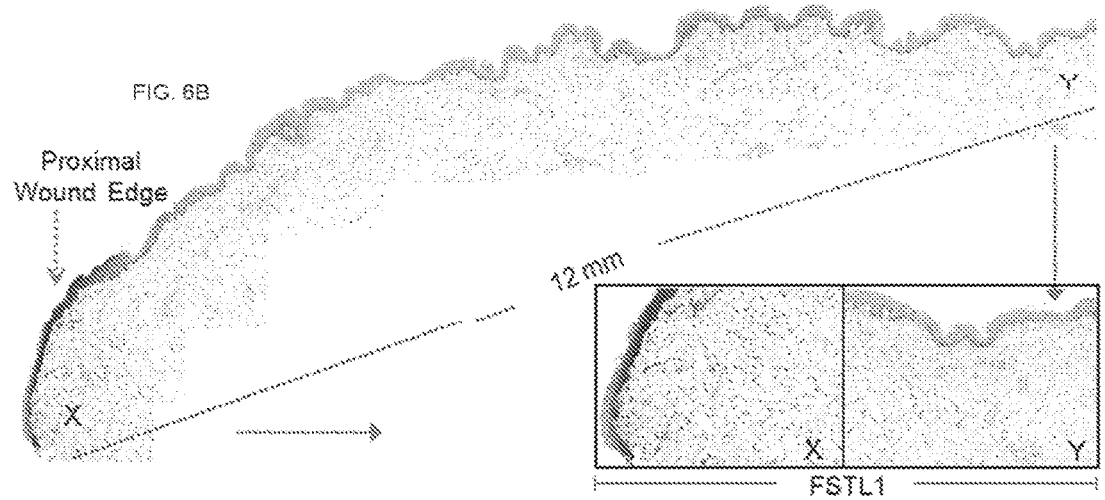
Figure 9A:
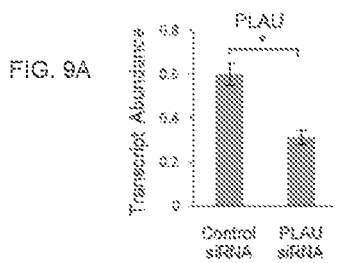
FIG. 9 a-f) shows quantification of mRNA and confirmation by immunocytochemistry using respective antibodies to assess relative knockdown efficiencies of DIAPH1, PLAU and LAMC2 after transfection with specific siRNAs *P<0.05 (n=3) g) Representative images of migrating keratinocytes transfected with a control siRNA or DIAPH1, PLAU or LAMC2 specific siRNA at the indicated time points after scratch wound (n=3). h-j) Histogram representing relative wound closure in a scratch wound assay. By 24 hours, knock-down of DIAPH1, PLAU and LAMC2 resulted in 46±16%, 59±8% and 40±6% respectively, compared to complete wound closure in control siRNA transfected cells (n=3). **P<0.001. Error bars represent s.d. Thus.
Figure 9B:
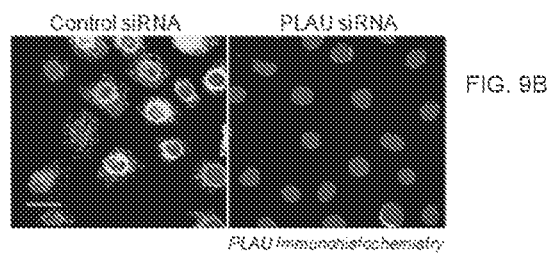
Figure 9C:
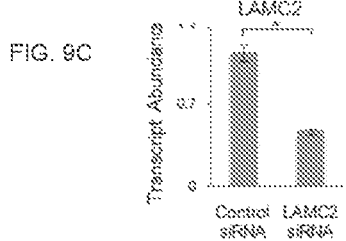
Figure 9D:
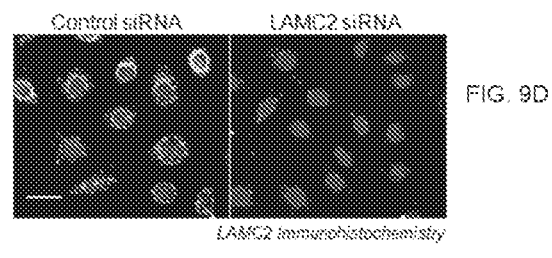
Figure 9E:
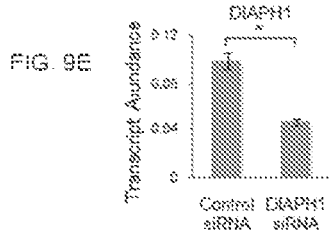
Figure 9F:
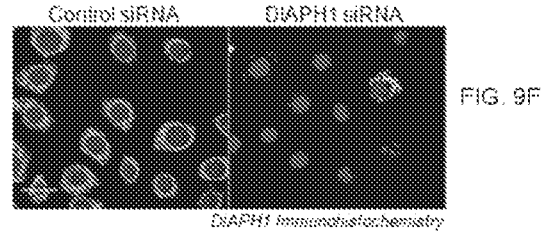
Figure 9G:
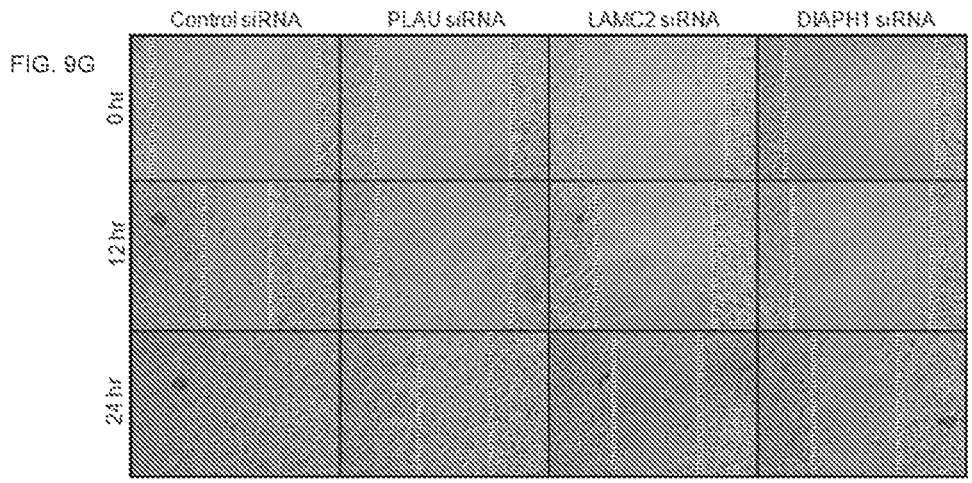
Figure 9H:
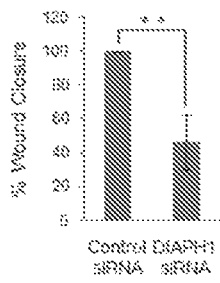
Figure 9I:
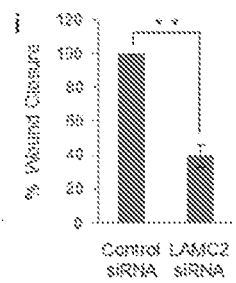
Figure 9J:
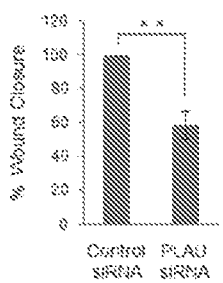
Figure 14:
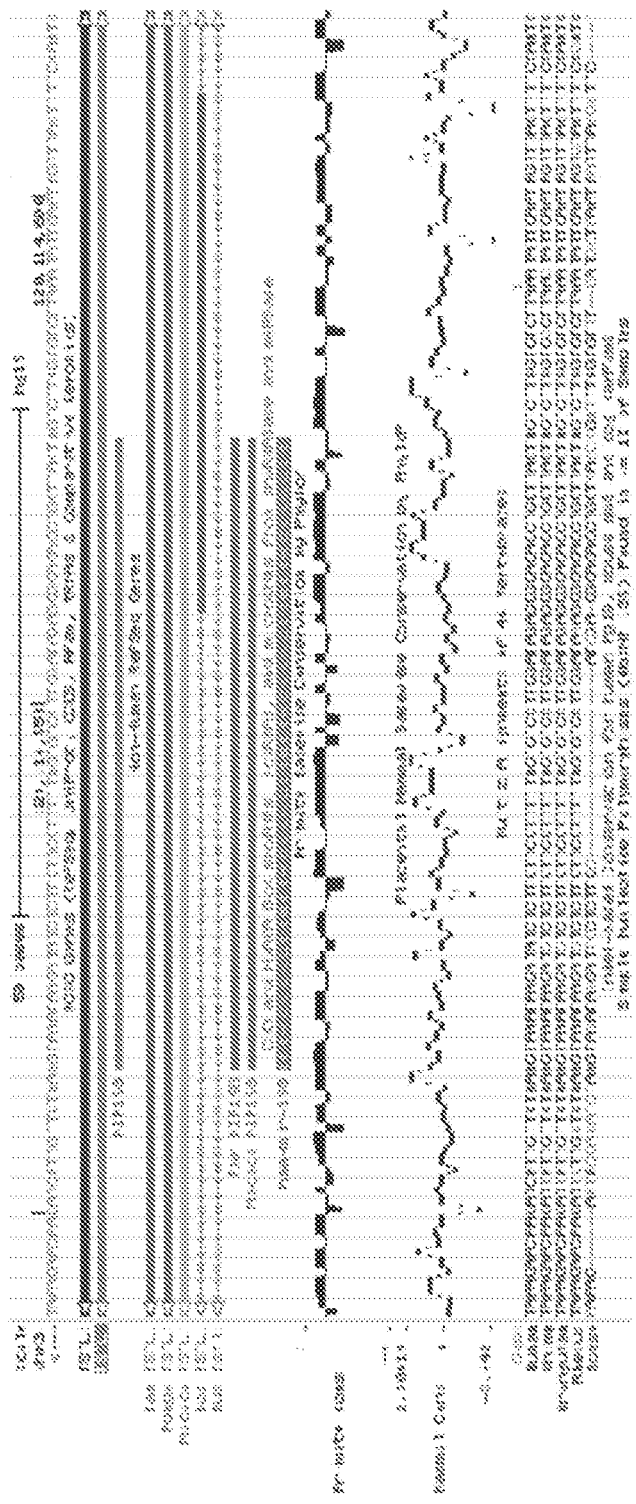
FIG. 14 shows a conservation map that clearly indicates miR-198 to be primate-specifically conserved as seen across primates and mammals. Pan-Chimpanzee, Pongo-Orangutan, Macaca-Rhesus macaque, Bos-Cattle and Mus-Mouse (SEQ ID NOs:72-77). Multi alignment with primates and mouse orthologous sequence shows the lack of conservation in mouse.

Differential miRNA expression profiling comparing miRNA from cutaneous wounds, using a human skin er vivo organ culture system sampled at 0 hours and 24 hours post-injury, revealed miR-198 as a consistent and significant differentially-expressed miRNA that is down-regulated upon injury. miR-198 is located within the eleventh exon of the protein-coding gene FSTL1, and belongs to a small number of human exonic miRNA stem-loops located in the 3'-untranslated region (FIG. 1a, FIG. 14). The full length FSTL1 transcript with the miR-198 stem-loop in cis can function either as a pri-miRNA transcript or as FSTL1 mRNA. In uninjured normal skin, the epidermis expresses high levels of miR-198. However upon cutaneous injury, miR-198 is significantly down-regulated as early as 3 hours after injury and by 24 hours following injury miR-198 is undetectable (FIG. 1b). In addition, in situ hybridization reveals the expression of mature miR-198 in epidermal keratinocytes in normal skin, but not in epidermis examined at 24 hours post-injury (FIG. 1c). The detection of low levels of pri-miRNA transcripts by semi-quantitative RT-PCR (FIG. 5c)

and localization of these transcripts in the nucleus observed by in-situ hybridization (FIG. 5d, left panel) at 0 hour post-injury suggests that mature miR-198 is indeed processed from this pri-miRNA. At 0 hour post-injury efficient nuclear miR-198 processing prevents nuclear export of pri-miRNA resulting in little or no FSTL1 protein expression (FIG. 5d-middle panel). However, FSTL1 protein expression was apparent in the epidermis 24 hours post-injury (FIG. 1e, 5d-last panel) indicating inefficient nuclear miR-198 processing and export of the pri-miRNA. Concomitant down-regulation of mature miR-198 was clearly observed (FIG. 1b, 1c) coupled with an increase in pri-miRNA transcript that now functions as FSTL1 mRNA (FIG. 5c) Explant wound experiments reveal a gradient of miR-198 disappearance and a concomitant appearance of FSTL1 from the proximal wound edge 24 hours post-injury (FIG. 6).

Figure 15:
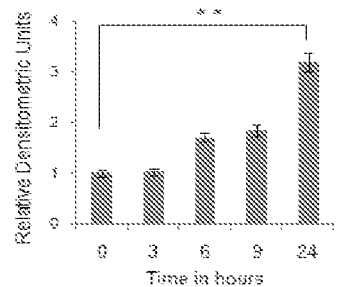
FIG. 15 shows densitometric analysis of band intensities from (FIG. 1d), normalized against RPLP0 intensity values. **P<0.001. Error bars represent s.d. Thus.
Figure 16A:
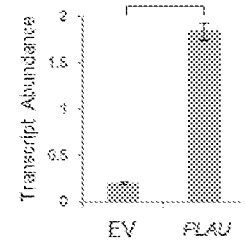
FIG. 16 a-c) shows histogram representing the relative transcript abundance of miR-198 targets in keratinocytes transfected with a control vector (EV) or constructs over-expressing DIAPH1, LAMC2 and PLAU. d-g) shows relative wound closure in keratinocytes co-transfected with miR-198 mimic and vectors over-expressing PLAU, LAMC2 or DIAPH1 individually or in combination (PLD) in equal ratios (n=3). *P<0.05, **P<0.001. Error bars represent s.d. Thus.
Figure 16B:
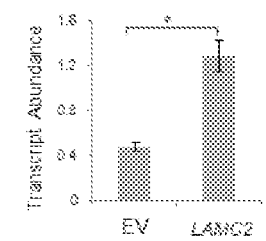
Figure 16C:
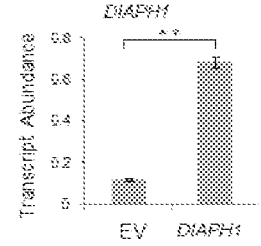
Figure 16D:
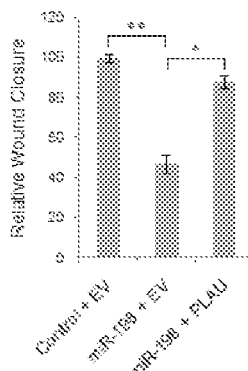
Figure 16E:
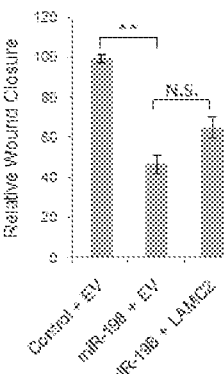
Figure 16F:
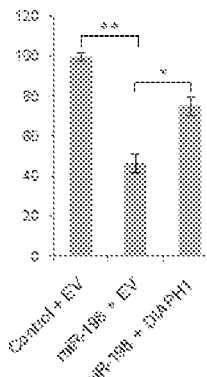
Figure 16G:
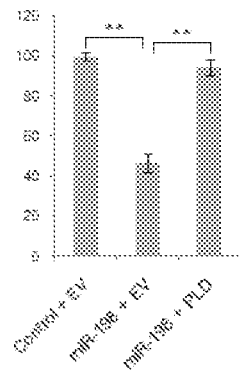

To address whether the presence of this miR-198 stem-loop in cis interferes with the expression of the linked protein coding gene, FSTL1 3'-UTR chimeric luciferase constructs was generated with or without miR-198 precursor. Equal translational efficiency of both the transcripts suggests that a miRNA stem-loop precursor located in the 3'-UTR of FSTL1 mRNA does not necessarily block expression of FSTL1 protein expression (FIGS. 5e, 5f). In conclusion, if pri-miR-198 transcript is not processed to miR-198, the full length transcript exported to the cytoplasm can function as an FSTL1 mRNA and express the encoded protein. Expression of miR-198 and absence of FSTL1 in steady-state epidermis, and their reciprocal expression following injury, indicates a post-transcriptional switch controlling the mutually exclusive, spatio-temporal expression of miR-198 and FSTL1 protein in different physiological states.

miR-198 lies within an exon of the FSTL1 gene, we investigated whether miR-198 and FSTL1 were being co-regulated. In contrast to miR-198, FSTL1 mRNA and protein were observed in the wound edge epidermis at 24 hours post-injury, but were not seen in unwounded epidermis (FIGS. 1d, 15, 1e). A reducing gradient of miR-198 intensity, and a corresponding appearance of FSTL1 protein, was observed from the wound edge out to about 12 mm (FIG. 6). A single transcript can therefore function either as a pri-miRNA transcript making miR-198 or as an mRNA8 producing FSTL1 protein, suggesting a post-transcriptional switch regulating context-specific expression of these diverse products of a single gene.

Figure 5A:
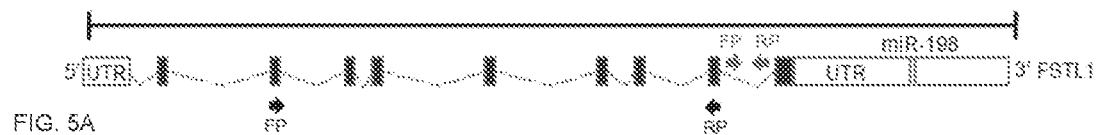
FIG. 5 a) shows a schematic of FSTL1 gene showing the exon-intron boundaries and the 3'-UTR sequence encoding the miR-198 precursor. Primers used in semi-quantitative RT-PCR below were designed to span specific exons coding for FSTL1 ORF as represented by the forward and reverse arrow marks. b) shows histogram representing quantification of pre-FSTL1 transcript using intron specific primers in normal versus injured skin (24 h after injury). N. S=not significant. c) shows representative semi-quantitative-RT-PCR analysis of FSTL1 mRNA using specific primers in explant samples after injury at indicated time points (n=3). d) shows in situ hybridization with oligo probes (panomics) on normal skin at 0 hours (left panel) reveals nuclear localization of FSTL1 mRNA that functions as pri-miRNA transcript. Immunohistochemical analysis of FSTL1 protein at (middle) 0 and (right) 24 hours after injury. (n=5) Scale bar=100 µM. e) shows a schematic diagram of the constructs used in luciferase assays. f) shows luciferase assays with chimeric luciferase constructs, containing FSTL1 3'-UTR with (~2.7 Kb from stop codon) or without the pre-miR-198 (~0.9 Kb from stop codon) (NS—not significant).
FIGS. 5e and 5f show that a miRNA stem-loop precursor located in the 3'-UTR of FSTL1 mRNA does not necessarily block expression of FSTL1 protein expression. In summary.
Figure 5B:
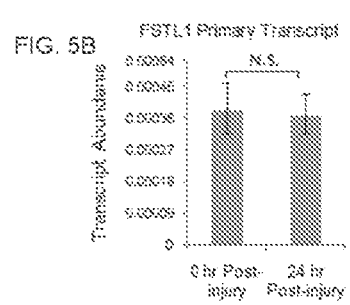
Figure 5E:
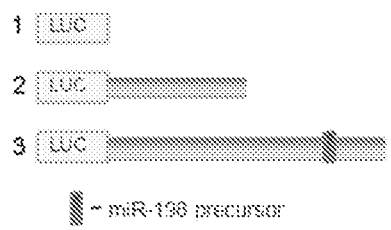
Figure 5F:
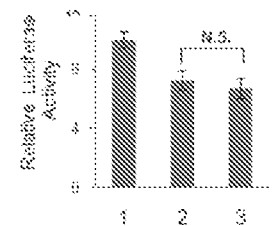

There was no significant change in expression of the primary FSTL1 transcript (the precursor of both pri-miRNA transcript and FSTL1 mRNA), confirming that regulation was post-transcriptional (FIG. 5a, b). Detection of low levels of pri-miRNA transcript (FSTL1 mRNA) at 0 hour post-injury (FIG. 5c), with transcript localization in the nucleus and absence of FSTL1 protein, indicated that the pri-miRNA transcript is processed to form mature miR-198 (FIG. 5d left and middle panel). Yet at 24 hours after injury, the pri-miRNA transcript is functioning as FSTL1 mRNA as confirmed by the abundant FSTL1 protein (FIG. 5d, right panel). The presence of the miRNA stem-loop precursor in the 3'-UTR of FSTL1 mRNA. does not inhibit FSTL1 protein expression, as confirmed by chimeric luciferase assays (FIG. 5e, 5f). In conclusion, if pri-miRNA transcript is not processed to miR-198, the full-length transcript is exported to the cytoplasm and functions as FSTL1 mRNA.

FSTL1 belongs to the BM-40/SPARC/osteonectin family of proteins containing both extracellular calcium-binding, follistatin-like domains, and often function as antagonists of the TGF-β related signaling pathways. However, unlike other activin antagonists, FST and FSTL3, FSTL1 expression is regulated by injury. FSTL1 is a glycoprotein that was originally cloned from an osteoblastic cell line as a TGF-β1 induced gene. Expression of FSTL1 protein in epidermis at the wound edge, but not in unwounded normal epidermal keratinocytes (FIGS. 1d and 1e and FIG. 15) prompted the present inventors to study the role of FSTL1 in keratinocyte migration. Keratinocytes transfected with siRNA against FSTL1 or control non-targeting siRNAs were grown to confluence as monolayers and subjected to scratch-wounding. Knock-down of FSTL1 (FIG. 7a, 7b) significantly suppressed migration of keratinocytes (FIG. 7 c, d) and only closed 15±5% of the scratch-wound area in 24 hours, compared to complete wound closure seen in keratinocytes transfected with control siRNAs (FIG. 7c). This demonstrated a novel role of FSTL1 in facilitating keratinocyte migration. Knock-down of FSTL1 (FIG. 7a, b) significantly suppressed migration of keratinocytes (FIG. 7c, d) demonstrating a new role for FSTL1 in promoting keratinocyte migration. Knock-down of FSTL1 did not affect miR-198 expression (FIG. 7e). Comparison of keratinocyte gene expression profiles in the presence and absence of FSTL1 revealed differentially expressed genes to include CXCL1010 and FERMT211, both essential for migration, suggesting pathways by which FSTL1 may increase keratinocyte migration (FIG. 7f).

In contrast, miR-198 expression in steady-state epidermis, and its down-regulation in activated migrating epidermal keratinocytes at the wound edge, suggests a function for miR-198 in inhibiting keratinocyte migration. Scratch wound assays were therefore used to examine migration in keratinocyte monolayers over-expressing miR-198 (FIG. 2a). Keratinocytes transfected with a non-targeting control sequence (control) were observed to close scratch wounds in 24 hours, whereas the keratinocytes transfected with miR-198 only closed 35±10% of the scratch-wound area in the same time (FIG. 2b-d). Thus, miR-198 restrains keratinocyte migration. Proliferation of keratinocytes was unaffected by over-expression of miR-198 (FIG. 2d). Furthermore, although FSTL1 mRNA itself has a binding site for miR-198, over-expression of miR-198 did not affect FSTL1 expression (FIG. 2e), as verified by luciferase assays (FIG. 2f). Together, these results suggest that miR-198 inhibits keratinocyte migration independently of FSTL1.

To further elucidate the mechanism underlying the inhibition of keratinocyte migration by miR-198, the present study sought to identify targets of miR-198, by comparing gene expression profiles from keratinocytes transfected with either miR-198 or control. Representation of selected array data as a heat-map revealed differentially expressed genes (FIG. 2g). Decreased expression of specific genes upon ectopic expression of miR-198 identified these genes as potential targets of miR-198. qRT-PCR validation of these genes, indicates that the array profiles could be used to ascertain global and specific properties of miR-198 (FIG. 2h).

To understand the physiological context-specific role of miR-198 in repressing these genes, target gene expression was analysed in an injury model using human skin organ culture. In normal steady-state skin where the epidermal keratinocytes express high levels of miR-198, target genes are down-regulated. Upon wounding, an increase in the expression of these genes, with a corresponding down-regulation of miR-198, supports the hypothesis that miR-198 regulates the expression of this sub-set of genes (FIG. 3a). These organ culture results correlate well with the results from miR-198 over-expression in cultured keratinocytes substantiating the involvement of miR-198 in regulating the expression of these genes (FIG. 2g, 2h).

Figure 3B:
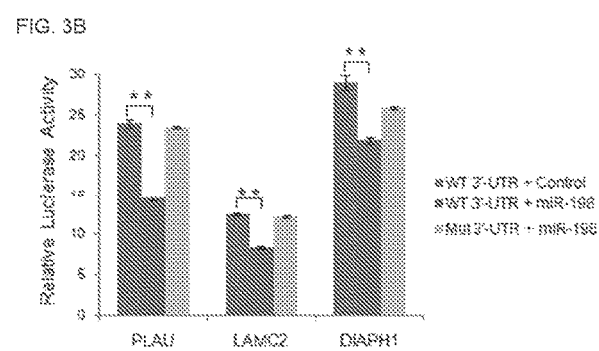

Interrogation of the Targetscan v5.1 database and correlation of the predicted interacting genes with microarray data revealed direct targets, each with at least one binding site for miR-198. The genes include urokinase-type plasminogen activator (PLAU), a serine protease involved in degradation of extracellular matrix components, diaphanous homolog 1 (DIAPH1), involved in actin polymerization and laminin gamma 2 chain (LAMC2), an essential component of the basement membrane protein laminin 5. To test the ability of miR-198 to negatively regulate PLAU, DIAPH1 and LAMC2 expression, chimeric 3'-UTR luciferase reporter assays was performed. Significant down-regulation of reporter activity with wild type PLAU, DIAPH1 and LAMC2 3'-UTR's, but not with mutant 3'-UTRs was clearly observed in the presence of ectopic miR-198, confirming these are direct targets of miR-198 (FIGS. 3B, 8). Knockdown of DIAPH1, PLAU and LAMC2 using gene-specific siRNA (FIG. 9a-f) significantly suppressed migration of keratinocytes and only closed 46±16%, 59±8% and 40±6% of the scratch-wound area in 24 hours, compared to complete wound closure seen in keratinocytes transfected with control siRNAs, thus phenocopying the effect of miR-198 (FIG. 9g-j). Although the present disclosure observed a moderate rescue of the effect of miR-198 with ectopic overexpression of individual targets, when taken in combination the rescue is highly significant (FIG. 16).

Figure 3C:
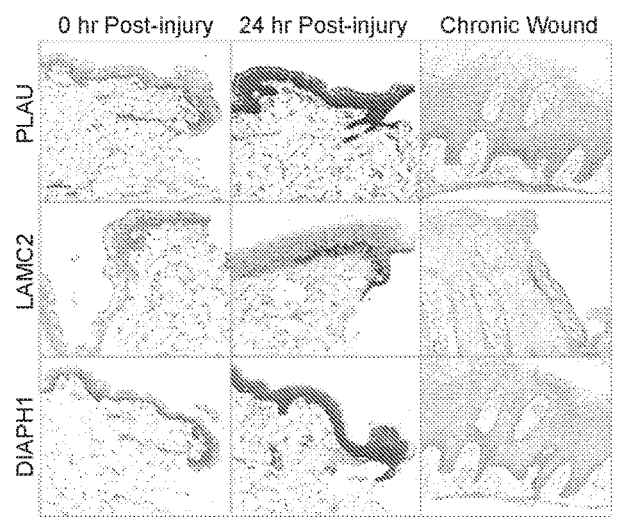

Protein expression from these target genes was tested by immunohistochemistry in normal healthy skin. Significant increase in the expression of these proteins in response to wounding was observed 24 hours after wounding, validating the mRNA expression profiles (FIG. 3c, left and middle panels). Expression of PLAU, LAMC2 and DIAPH1 protein in epidermis at the wound edge, but not in unwounded normal epidermal keratinocytes (FIG. 3c) highlights a role for these proteins in keratinocyte migration. This demonstrates a vital role of miR-198 in targeting these genes and inhibiting keratinocyte migration in steady-state normal skin.

Figure 3D:
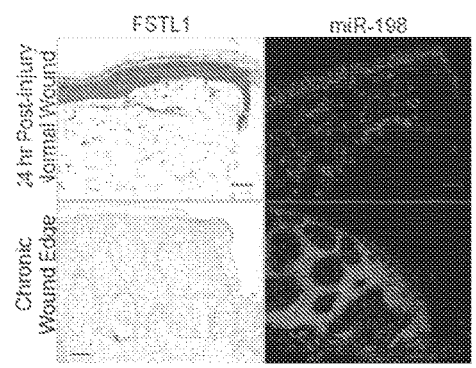
Figure 10:
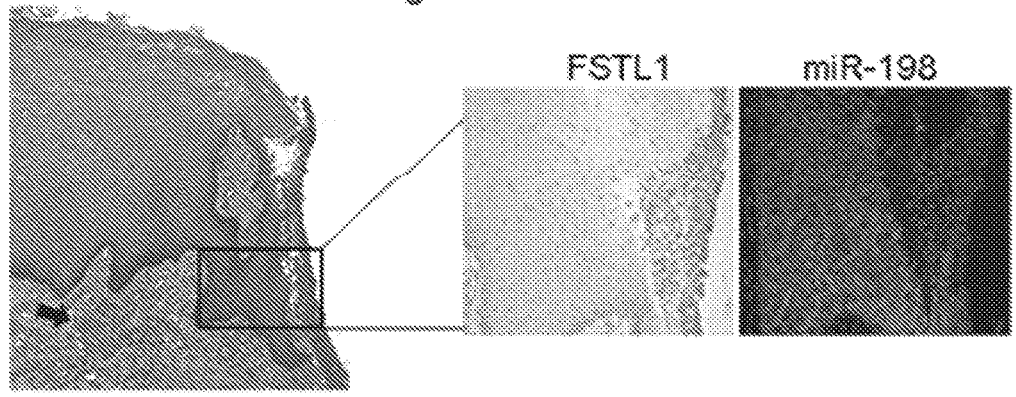
FIG. 10 shows tissue sections of chronic diabetic wounds stained with haematoxylin and eosin. Arrow and box indicates granulation tissue and wound edge respectively. Immunohistochemistry with FSTL1 antibody (left), or in situ hybridization with miR-198 probe (right), showing high levels of miR-198, but no FSTL1 protein at the wound edge of non-healing wounds. Thus.

The present study then investigated the expression of these targets in chronic non-healing ulcer wounds from patients with diabetes mellitus, where wound healing is defective. In contrast to normal healing wounds, a lower expression of PLAU, DIAPH1 and LAMC2 was observed in chronic diabetic ulcer wounds (FIG. 3c, right panel). Persistent high levels of miR-198 detected in the epidermal keratinocytes at the wound edge of chronic diabetic ulcers (n=8) explained the absence or low levels of its target genes (FIG. 3d). Furthermore, absence of FSTL1 protein in the wound edge of chronic diabetic ulcers suggests a defective miR-198/FSTL1 post-transcriptional switch in chronic diabetic ulcers (FIG. 3d and FIG. 10).

In an attempt to understand the regulation of the post-transcriptional switch that determines the fate of a transcript to function as a pri-miRNA or a mRNA, the sequence of miR-198 stem-loop precursor in the 3'-UTR of FSTL1 transcript was analysed. The presence of a GUG motif (FIG. 1A) within the terminal loop suggests that miR-198 belongs to a cohort of miRNAs processed by KSRP that binds to the specific G-rich motif. RNA-binding protein immunoprecipitation (RIP) (FIG. 4a and FIG. 11a) and RNA gel retardation assay (FIG. 4b and FIG. 11b) confirmed the binding of KSRP to the GUG motif of pri-miR-198 transcript in epidermal keratinocytes. Mutation of the G-rich motif in the loop results in the abrogation of RNA-protein complex formation, highlighting the specificity of binding. Further, efficient processing of miR-198 in the presence of recombinant KSRP confirms the role of KSRP in the processing of miR-198 (FIG. 4c). Up-regulation of pri-miRNA/FSTL1 transcripts upon knock-down of KSRP with a corresponding decrease in mature miR-198 expression highlights the role of KSRP in regulating miR-198/FSTL1 switch (FIG. 4E). This suggests that the mere presence of a miR-198 precursor stem-loop in cis cannot efficiently induce nuclear miR-198 processing. Adding another layer of complexity, the processing of exonic miR-198 was demonstrated to be dependent on a trans-acting RNA-binding protein KSRP. In the absence of nuclear localized KSRP, inefficient processing of pri-miRNA-198 transcripts results in the export of pri-miRNA-198/FSTL1 to the cytoplasm and expresses the encoded protein FSTL1.

Formation of an RNA-protein complex with the wild-type probe (GUG motif), but not with a mutant probe (CUC motif), confirms the specificity of binding. Addition of recombinant KSRP to an in vitro miRNA processing assay yielded a significant increase in mature miR-198 with wild-type (GUG motif) but not with mutant (CUC motif) sequences, confirming the role of KSRP in miR-198 processing (FIG. 4c, d).

In loss-of function assays using a gene-specific siRNA against KSRP, detection of low levels of mature miR-198 with a corresponding increase in the pri-miRNA transcript (now functioning as FSTL1 mRNA) supports the essential role of KSRP in switching-on miR-198 processing (FIG. 4d). This suggests that the mere presence of a miR-198 precursor stem-loop in cis cannot efficiently induce nuclear miR-198 processing. Adding another layer of complexity, the present study demonstrates that processing of exonic miR-198 is dependent on a trans-acting RNA-binding protein, KSRP1. In the absence of KSRP, miR-198 processing fails and the pri-miRNA transcript now functions as FSTL1 mRNA, resulting in expression of the FSTL1 protein.

Figure 12A:
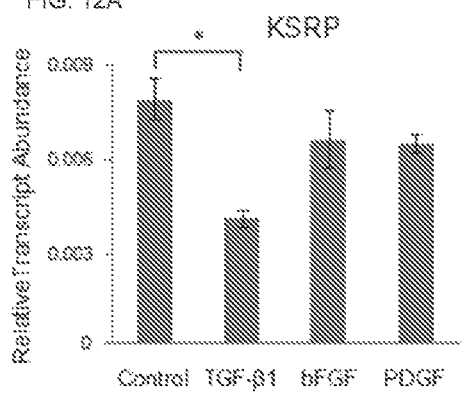
FIG. 12 a) shows relative transcript abundance of KSRP in keratinocytes treated with TGF-β1, FGF2 and PDGF-AB for 24 hrs as measured by qRT-PCR *P<0.05. b) shows immunocytochemistry staining using KSRP-specific antibody shows a decrease in KSRP protein expression in TGF-β1 treated cells. c) shows relative transcript abundance of FSTL1 in keratinocytes treated with TGF-β1, FGF2 and PDGF-AB for 24 hrs as measured by qRT-PCR. *P<0.05. Student's t-test was used to calculate P value and error bars denote mean±s.e.m. d) shows immunocytochemistry staining using FSTL1-specific antibody shows increased FSTL1 protein expression in TGF-β1 treated cells (n=3). Thus.
Figure 12B:
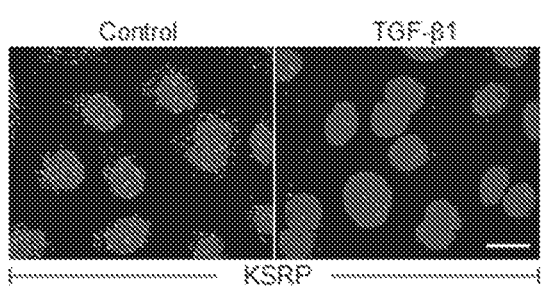
Figure 12C:
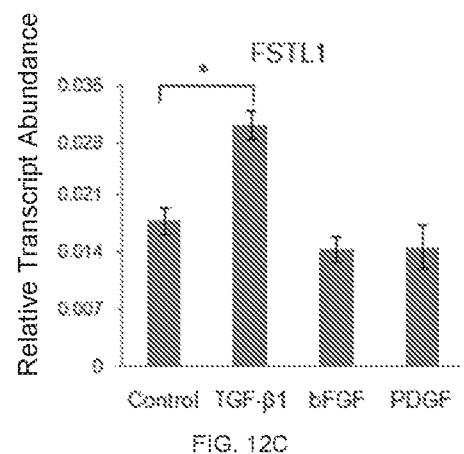
Figure 12D:
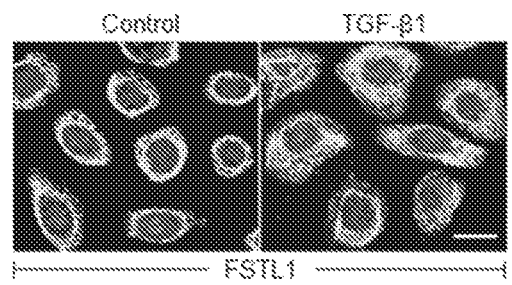

The study then sought to identify the signaling mechanism that directly controls KSRP expression and indirectly regulates the post-transcriptional switch. Treatment with TGF-β1, but not other growth factors involved in wound healing such as FGF2 and PDGF-AB (FIG. 12c, 12d), switched on the expression of FSTL1 in keratinocytes with a corresponding specific down-regulation of KSRP but not another abundant RNA-binding protein HUR (FIG. 4f, 12a, 12b). The role of TGF-β1 in altering the localization of KSRP from nucleus to cytoplasm further confirms the link between TGF-β1 and KSRP. Additionally in keratinocytes TGF-β1 induced the expression of miR-181a with a concomitant down-regulation of KSRP (FIG. 13a). KSRP is a direct target of miR-181a with a highly conserved binding site in the 3'-UTR. As a TGF-β1 induced gene, miR-181a is detected as early as 3-hours post-injury and up-regulated significantly after 9 hours post-injury (FIG. 13b). This suggests that TGF-β1 may repress KSRP expression by a post-transcriptional miR-181a-mediated regulatory mechanism. Together this data suggests that in normal epidermal keratinocytes, miR-198 is processed by KSRP, but upon injury paracrine TGF-β1 signaling blocks expression of miR-198 by down-regulating KSRP (FIGS. 4a, 4g), thus facilitating the expression of FSTL1. This is supported by the detection of elevated levels of TGF-β1 in normal injury with a corresponding down-regulation of KSRP (FIG. 4g and FIG. 12b). This raises the likelihood that the low levels of TGF-β and absence of TGF-β1 receptors in chronic wounds may directly contribute to constitutive expression of miR-198. Supporting this argument significantly higher expression of KSRP and low levels of TGF-β1 in chronic diabetic ulcers was observed (FIG. 4g). In conclusion, a non-functional switch leads to constitutive expression of miR-198, an inhibitor of keratinocyte migration and prevents expression of FSTL1 essential for keratinocyte migration. This non-functional switch is the cause for impaired keratinocyte migration and loss of re-epithelialization culminating in non-healing chronic wounds; a consequence of defective TGF-β signaling.

Increase in transcript abundance of miR-198 targets and FSTL1 are independent of de novo transcription, as was confirmed by actinomycin-D inhibition of transcription (FIGS. 17a 17b, 18a and 18b). Thus TGF-β1 signalling promotes transcript stability of FSTL1 and miR-198 targets.

Figure 17A:
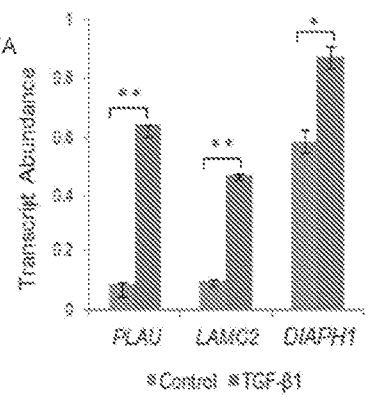
FIG. 17 a) shows histogram representing relative transcript abundance of PLAU, LAMC2 and DIAPH1 in keratinocytes treated with TGF-β1. b) shows histogram representing relative transcript abundance of PLAU, LAMC2 and DIAPH1 in keratinocytes treated with TGF-β1 in the presence of actinomycin-D. c) shows relative transcript abundance of DROSHA and PLAU, LAMC2 and DIAPH1 in keratinocytes transfected with a non targeting siRNA or siRNA against DROSHA. *P<0.05, P<0.001. Student's t-test was used to calculate P value and error bars denote mean±s.e.m. d) shows immunocytochemistry for PLAU, LAMC2 and DIAPH1 on keratinocytes transfected with a control inhibitor or LNA inhibitor for mature miR198 shows a specific upregulation of miR-198 targets after inhibition of miR-198 (n=3). Thus.
Figure 17B:
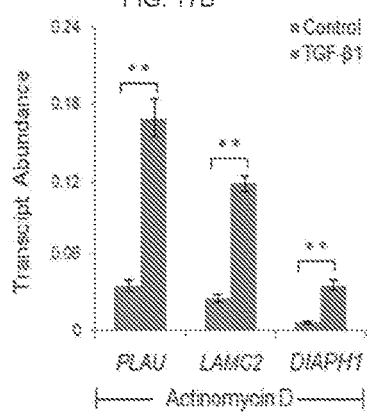
Figure 17C:
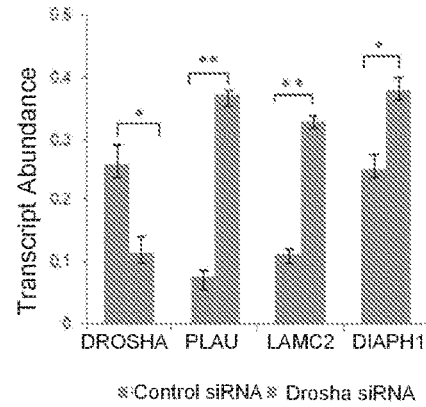
Figure 17D:
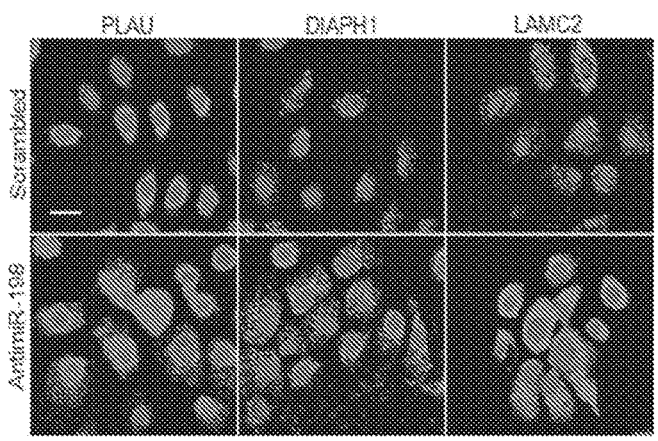

Blocking the processing of miR-198 using siRNA against Drosha leads to an increase in transcript abundance of miR-198 targets and FSTL1 (FIGS. 17c, 18c and 18d). Functional inhibition of miR-198 with antimiR-198 results in increased protein expression of targets (FIG. 17d). However, no change in FSTL1 expression with antimiR-198 (FIG. 18e) confirms that FSTL1 is not a target of miR-198. In summary, TGF-β1 promotes the stability of FSTL1 by down-regulating KSRP, which is essential for miR-198 processing, providing a mechanism for post-transcriptional regulation of FSTL1 and miR-198 target mRNAs.

The KSRP 3'-UTR has a highly conserved binding site for miR-181a17, a TGF-β1 induced miRNA (FIG. 13a). A concomitant down-regulation of KSRP suggests a link between TGF-β1 and KSRP mediated by miR-181a. Detection of miR-181a as early as 3 hours post-injury in explant wound assays suggested that repression of KSRP by TGF-β1 is potentially mediated by miR-181a (FIG. 13b). Significant down-regulation of luciferase activity upon co-transfection with miR-181a and wild-type (but not mutant) KSRP 3'-UTR confirmed that KSRP is a direct target of miR-181a (FIG. 13c). This link between KSRP and TGF-β1 is further supported by the detection of KSRP in normal epidermal keratinocytes in the absence of TGF-β1 (FIG. 3e, left panel). However, upon injury TGF-β1 down-regulates KSRP (FIG. 3e, middle panel), thus facilitating the expression of FSTL1. This suggests that the observed low levels of TGF-1 and absence of TGF-1 receptors in chronic wounds may directly contribute to constitutive expression of miR-198. Supporting this argument the present study observed significantly higher expression of KSRP and low levels of TGF-β1 in chronic wounds (FIG. 4g, right panel). Thus the dysfunctional FSTL1-miR-198 switch that is the potential cause of impaired keratinocyte migration and loss of re-epithelialization culminating in non-healing chronic wounds may be a consequence of defective TGF-β signaling.

Wound healing is a well-coordinated, progressive series of events designed to restore the barrier function and integrity of the skin. Keratinocyte migration and re-epithelialization is an essential process for the early phase of wound healing, when rapid wound closure is critical to prevent infection and water loss. During migration, the basal and suprabasal cells of the epidermis contribute to re-epithelialization by active sheet migration driven by actin polymerization. Data presented here show that post-transcriptional regulon is directly involved in controlling keratinocyte migration. At homeostasis, a cross-section of epidermal genes required for keratinocyte activation and migration are kept silent by the presence of miR-198. By suppressing DIAPH1, which is important for actin polymerization, migration of keratinocytes can be hindered. This demonstrates a novel role of DIAPH1 in keratinocyte migration. Inappropriate expression of miR-198 may not only restrict migration but could also contribute to decreased fibrinolysis and impaired matrix deposition in chronic diabetic ulcers by inhibiting the expression of PLAU. After initiation of migration, the keratinocytes moving over the wound bed must produce new basement membrane components including laminin 5, which is essential for wound re-epithelialization. By repressing expression of LAMC2, miR-198 could impede re-epithelialization. At the non-healing edge of diabetic ulcers, keratinocytes display hyperproliferation but fail to migrate (FIG. 4A). Data as presented herein suggests that failure to switch off miR-198 results in failure of these wounds to heal: by inhibiting multiple genes involved in various facets of keratinocyte migration, miR-198 may effectively prevent cell migration and re-epithelialization in chronic diabetic wounds (FIG. 4G). The present disclosure demonstrates, a hither-to unknown function of FSTL1 in promoting keratinocyte migration and proposes how absence of FSTL1, a consequence of defective switch, can hinder re-epithelialization in chronic diabetic wounds.

In conclusion, the present disclosure report a post-transcriptional regulon controlled by paracrine TGF-β-signaling that is essential for normal wound healing. A defective, non-functional switch may perturb cellular responses, in particular wound-responsive keratinocyte migration and re-epithelialization, leading to chronic non-healing wounds. The use of increasingly complex human keratinocyte tissue mimetic systems to analyze wound healing has thus helped identify a novel mechanism which appears to be critical for wound healing, and identifies miR-198 as a potential molecular biomarker for non-healing wounds and an important therapeutic target for treatment of chronic diabetic ulcers. Targeting miR-198 and administering FSTL1 polypeptides in wound healing disorders would be useful as combinatorial topical therapeutics used to improve patient outcomes.

The invention claimed is:

1. A method of promoting wound healing or wound closure, wherein the method comprises administration of a miR-198 inhibitor and a follistatin-like-1 (FSTL1) polypeptide.

2. A method of treating chronic cutaneous wounds, wherein the method comprises administration of a miR-198 inhibitor and a follistatin-like-1 (FSTL1) polypeptide.

3. The method of claim 1, further comprising administration of TGF-β1 either simultaneously or before or after administration of the miR-198 inhibitor and the FSTL1 polypeptide.

4. The method of claim 1, wherein in case miR-198 inhibitor and follistatin-like-1 (FSTL1) polypeptide are administered simultaneously or separately from each other.

5. The method of claim 2, wherein the chronic cutaneous wounds are the wounds of a patient suffering or suspected to be suffering from diabetes mellitus.

6. The method of claim 2, wherein the chronic cutaneous wound is diabetic ulcer.

7. The method of claim 1, wherein administration is via systemic or topical administration.

8. The method of claim 7, wherein administration is via topical administration.

9. The method of claim 1, wherein the miR-198 inhibitor and FSTL1 polypeptide are administered independently of each other in an amount of between about 10 μg to 300 mg/kg body weight.

10. The method of claim 1, wherein TGF-β1 is administered in an amount of between about 10 μg to 300 mg/kg body weight.

11. The method of claim 1, wherein the miR-198 inhibitor is selected from the group of an anti-miR-198, peptide nucleic acid (PNA) derivatives of miR-198 inhibitor sequence and Tiny LNA anti-miRs for seed-sequence of the inhibitor.

12. The method of claim 1, wherein the miR-198 inhibitor has the sequence: 5'-GAACCUAUCUCCCCUCUGGACC-3' (SEQ ID NO: 1).

13. The method of claim 12, wherein the inhibitor is unmodified.

14. The method of claim 12, wherein the inhibitor is with at least one modification/s selected from the group consisting of 1) full or partial 2'-O-methoxy ethyl modification, 2) full or partial phosphorothioate modification, 3) cholesterol modification of 3' end of the miR-198 inhibitor and 4) full or partial locked nucleic acid modification (LNA) of nucleotides.

* * * * *

UNITED STATES PATENT AND TRADEMARK OFFICE
CERTIFICATE OF CORRECTION

PATENT NO. : 9,545,420 B2
APPLICATION NO. : 14/417763
DATED : January 17, 2017
INVENTOR(S) : Prabha Sampath Page 1 of 1

It is certified that error appears in the above-identified patent and that said Letters Patent is hereby corrected as shown below:

On the Title Page

Item (30), "Foreign Application Priority Data", in Column 1, Line 1, delete "201205614" and insert --201205614-9--, therefor In the Claims In Column 57, Line 13, in Claim 4, after "in", delete "case"

Signed and Sealed this
Tenth Day of April, 2018

Andrei Iancu
*Director of the United States Patent and Trademark Office*

SEQUENCE LISTING

<160> NUMBER OF SEQ ID NOS: 64

<210> SEQ ID NO 1
<211> LENGTH: 22
<212> TYPE: DNA
<213> ORGANISM: Artificial sequence
<220> FEATURE:
<223> OTHER INFORMATION: A synthetic oligonucleotide miR-198 inhibitor

<400> SEQUENCE: 1
gaaccuaucu ccccucugga cc                    22

```
<210> SEQ ID NO 2
<211> LENGTH: 308
<212> TYPE: PRT
<213> ORGANISM: Homo sapiens

<400> SEQUENCE: 2

Met Trp Lys Arg Trp Leu Ala Leu Ala Leu Ala Val Ala Val
1               5                   10                  15

Trp Val Arg Ala Glu Glu Leu Arg Ser Lys Ser Lys Ile Cys Ala
        20                  25                  30

Asn Val Phe Cys Gly Ala Gly Arg Glu Cys Ala Val Thr Glu Lys Gly
            35                  40                  45

Glu Pro Thr Cys Leu Cys Ile Glu Gln Cys Lys Pro His Lys Arg Pro
    50                  55                  60

Val Cys Gly Ser Asn Gly Lys Thr Tyr Leu Asn His Cys Glu Leu His
65                  70                  75                  80

Arg Asp Ala Cys Leu Thr Gly Ser Lys Ile Gln Val Asp Tyr Asp Gly
                85                  90                  95

His Cys Lys Glu Lys Lys Ser Val Ser Pro Ser Ala Ser Pro Val Val
            100                 105                 110

Cys Tyr Gln Ser Asn Arg Asp Glu Leu Arg Arg Ile Ile Gln Trp
            115                 120                 125

Leu Glu Ala Glu Ile Ile Pro Asp Gly Trp Phe Ser Lys Gly Ser Asn
130                 135                 140

Tyr Ser Glu Ile Leu Asp Lys Tyr Phe Lys Asn Phe Asp Asn Gly Asp
145                 150                 155                 160

Ser Arg Leu Asp Ser Ser Glu Phe Leu Lys Phe Val Glu Gln Asn Glu
                165                 170                 175

Thr Ala Ile Asn Ile Thr Thr Tyr Pro Asp Gln Glu Asn Asn Lys Leu
            180                 185                 190

Leu Arg Gly Leu Cys Val Asp Ala Leu Ile Glu Leu Ser Asp Glu Asn
        195                 200                 205

Ala Asp Trp Lys Leu Ser Phe Gln Glu Phe Leu Lys Cys Leu Asn Pro
210                 215                 220

Ser Phe Asn Pro Pro Glu Lys Lys Cys Ala Leu Glu Asp Glu Thr Tyr
225                 230                 235                 240

Ala Asp Gly Ala Glu Thr Glu Val Asp Cys Asn Arg Cys Val Cys Ala
                245                 250                 255

Cys Gly Asn Trp Val Cys Thr Ala Met Thr Cys Asp Gly Lys Asn Gln
            260                 265                 270

Lys Gly Ala Gln Thr Gln Thr Glu Glu Met Thr Arg Tyr Val Gln
        275                 280                 285

Glu Leu Gln Lys His Gln Glu Thr Ala Glu Lys Thr Lys Arg Val Ser
        290                 295                 300

Thr Lys Glu Ile
305

<210> SEQ ID NO 3
<211> LENGTH: 62
<212> TYPE: DNA
<213> ORGANISM: Homo sapiens

<400> SEQUENCE: 3
tcattggtcc agaggggaga taggttcctg tgattttcc ttcttctcta tagaataaat    60
ga                                                                 62
```

```
<210> SEQ ID NO 4
<211> LENGTH: 62
<212> TYPE: RNA
<213> ORGANISM: Homo sapiens

<400> SEQUENCE: 4
ucauuggucc agaggggaga uagguuccug ugauuuuucc uucuucucua uagaauaaau      60
ga                                                                    62

<210> SEQ ID NO 5
<211> LENGTH: 22
<212> TYPE: DNA
<213> ORGANISM: Homo sapiens

<400> SEQUENCE: 5
ggtccagagg ggagataggt tc                                              22

<210> SEQ ID NO 6
<211> LENGTH: 22
<212> TYPE: RNA
<213> ORGANISM: Homo sapiens

<400> SEQUENCE: 6
gguccagagg ggagauaggu uc                                              22

<210> SEQ ID NO 7
<211> LENGTH: 62
<212> TYPE: DNA
<213> ORGANISM: Homo sapiens

<400> SEQUENCE: 7
tcatttattc tatagagaag aaggaaaaat cacaggaacc tatctcccct ctggaccaat      60
ga                                                                    62

<210> SEQ ID NO 8
<211> LENGTH: 62
<212> TYPE: RNA
<213> ORGANISM: Homo sapiens

<400> SEQUENCE: 8
ucauuuauuc uauagagaag aaggaaaaau cacaggaacc uaucuccccu cuggaccaau      60
ga                                                                    62

<210> SEQ ID NO 9
<211> LENGTH: 22
<212> TYPE: DNA
<213> ORGANISM: Homo sapiens

<400> SEQUENCE: 9
gaacctatct cccctctgga cc                                              22

<210> SEQ ID NO 10
<211> LENGTH: 22
<212> TYPE: RNA
<213> ORGANISM: Homo sapiens

<400> SEQUENCE: 10
gaaccuaucu cccctcugga cc                                              22
```

```
<210> SEQ ID NO 11
<211> LENGTH: 21
<212> TYPE: DNA
<213> ORGANISM: Artificial sequence
<220> FEATURE:
<223> OTHER INFORMATION: A synthetic oligonucleotide FSTL1 3'-UTR
<220> FEATURE:
<221> NAME/KEY: misc_feature
<223> OTHER INFORMATION: forward primer

<400> SEQUENCE: 11
gagttggccc tgtctcttct t                                              21

<210> SEQ ID NO 12
<211> LENGTH: 21
<212> TYPE: DNA
<213> ORGANISM: Artificial sequence
<220> FEATURE:
<223> OTHER INFORMATION: A synthetic oligonucleotide FSTL1 3'-UTR
      reverse primer

<400> SEQUENCE: 12
ctttcccact ctcttcctgc t                                              21

<210> SEQ ID NO 13
<211> LENGTH: 21
<212> TYPE: DNA
<213> ORGANISM: Artificial sequence
<220> FEATURE:
<223> OTHER INFORMATION: A synthetic oligonucleotide FSTL1 ORF
<220> FEATURE:
<221> NAME/KEY: misc_feature
<223> OTHER INFORMATION: forward primer

<400> SEQUENCE: 13
aatccaagat ctgtgccaat g                                              21

<210> SEQ ID NO 14
<211> LENGTH: 21
<212> TYPE: DNA
<213> ORGANISM: Artificial sequence
<220> FEATURE:
<223> OTHER INFORMATION: A synthetic oligonucleotide FSTL1 ORF reverse
      primer

<400> SEQUENCE: 14
gctgtacaga cccaatttcc a                                              21

<210> SEQ ID NO 15
<211> LENGTH: 21
<212> TYPE: DNA
<213> ORGANISM: Artificial sequence
<220> FEATURE:
<223> OTHER INFORMATION: A synthetic oligonucleotide FSTL1 primary
      transcript forward primer

<400> SEQUENCE: 15
gggatctctg ggaatggaat a                                              21

<210> SEQ ID NO 16
<211> LENGTH: 21
<212> TYPE: DNA
<213> ORGANISM: Artificial sequence
<220> FEATURE:
<223> OTHER INFORMATION: A synthetic oligonucleotide FSTL1 primary
      transcript reverse primer
```

```
<400> SEQUENCE: 16
acactgatag gccacaaatg c                                              21

<210> SEQ ID NO 17
<211> LENGTH: 21
<212> TYPE: DNA
<213> ORGANISM: Artificial sequence
<220> FEATURE:
<223> OTHER INFORMATION: A synthetic oligonucleotide ITGA3 foward primer

<400> SEQUENCE: 17
taaatggctg ggctacccta t                                              21

<210> SEQ ID NO 18
<211> LENGTH: 21
<212> TYPE: DNA
<213> ORGANISM: Artificial sequence
<220> FEATURE:
<223> OTHER INFORMATION: A synthetic oligonucleotide ITGA3 reverse
      primer

<400> SEQUENCE: 18
gggtccgctt aaagaagtca c                                              21

<210> SEQ ID NO 19
<211> LENGTH: 21
<212> TYPE: DNA
<213> ORGANISM: Artificial sequence
<220> FEATURE:
<223> OTHER INFORMATION: A synthetic oligonucleotide ISG20
<220> FEATURE:
<221> NAME/KEY: misc_feature
<223> OTHER INFORMATION: forward primer

<400> SEQUENCE: 19
tgagggagag atcaccgatt a                                              21

<210> SEQ ID NO 20
<211> LENGTH: 21
<212> TYPE: DNA
<213> ORGANISM: Artificial sequence
<220> FEATURE:
<223> OTHER INFORMATION: A synthetic oligonucleotide ISG20 reverse
      primer

<400> SEQUENCE: 20
gctcatgtcc tctttcagtg c                                              21

<210> SEQ ID NO 21
<211> LENGTH: 21
<212> TYPE: DNA
<213> ORGANISM: Artificial sequence
<220> FEATURE:
<223> OTHER INFORMATION: A synthetic oligonucleotide IRAK2
<220> FEATURE:
<221> NAME/KEY: misc_feature
<223> OTHER INFORMATION: forward primer

<400> SEQUENCE: 21
caagtgattc tcctgcctca g                                              21

<210> SEQ ID NO 22
<211> LENGTH: 21
<212> TYPE: DNA
<213> ORGANISM: Artificial sequence
```

```
<220> FEATURE:
<223> OTHER INFORMATION: A synthetic oligonucleotide IRAK2 reverse
      primer

<400> SEQUENCE: 22
tcaagcctgt aatcccaaca c                                            21

<210> SEQ ID NO 23
<211> LENGTH: 21
<212> TYPE: DNA
<213> ORGANISM: Artificial sequence
<220> FEATURE:
<223> OTHER INFORMATION: A synthetic oligonucleotide RSAD2 forward
      primer

<400> SEQUENCE: 23
gtgcctggat ttcatgtcag t                                            21

<210> SEQ ID NO 24
<211> LENGTH: 21
<212> TYPE: DNA
<213> ORGANISM: Artificial sequence
<220> FEATURE:
<223> OTHER INFORMATION: A synthetic oligonucleotide RSAD2 reverse
      primer

<400> SEQUENCE: 24
atgcttgctt tctctgagct g                                            21

<210> SEQ ID NO 25
<211> LENGTH: 21
<212> TYPE: DNA
<213> ORGANISM: Artificial sequence
<220> FEATURE:
<223> OTHER INFORMATION: A synthetic oligonucleotide LAMC2 forward
      primer

<400> SEQUENCE: 25
ctgggttgtg cacatttctt t                                            21

<210> SEQ ID NO 26
<211> LENGTH: 21
<212> TYPE: DNA
<213> ORGANISM: Artificial sequence
<220> FEATURE:
<223> OTHER INFORMATION: A synthetic oligonucleotide LAMC2 reverse
      primer

<400> SEQUENCE: 26
aaatacagaa gcaaggcagc a                                            21

<210> SEQ ID NO 27
<211> LENGTH: 21
<212> TYPE: DNA
<213> ORGANISM: Artificial sequence
<220> FEATURE:
<223> OTHER INFORMATION: A synthetic oligonucleotide LAMC2 ORF forward
      primer

<400> SEQUENCE: 27
agtggaagga gagctggaaa g                                            21

<210> SEQ ID NO 28
<211> LENGTH: 21
<212> TYPE: DNA
<213> ORGANISM: Artificial sequence
```

```
<220> FEATURE:
<223> OTHER INFORMATION: A synthetic oligonucleotide LAMC2 ORF reverse
      primer

<400> SEQUENCE: 28
gaccagcccc tcttcatcta c                                              21

<210> SEQ ID NO 29
<211> LENGTH: 21
<212> TYPE: DNA
<213> ORGANISM: Artificial sequence
<220> FEATURE:
<223> OTHER INFORMATION: A synthetic oligonucleotide PLAU forward primer

<400> SEQUENCE: 29
gcttgtccaa gagtgcatgg t                                              21

<210> SEQ ID NO 30
<211> LENGTH: 19
<212> TYPE: DNA
<213> ORGANISM: Artificial sequence
<220> FEATURE:
<223> OTHER INFORMATION: A synthetic oligonucleotide PLAU reverse primer

<400> SEQUENCE: 30
agggctggtt ctcgatggt                                                 19

<210> SEQ ID NO 31
<211> LENGTH: 21
<212> TYPE: DNA
<213> ORGANISM: Artificial sequence
<220> FEATURE:
<223> OTHER INFORMATION: A synthetic oligonucleotide PLAU ORF forward
      primer

<400> SEQUENCE: 31
tcactggctt tggaaaagag a                                              21

<210> SEQ ID NO 32
<211> LENGTH: 21
<212> TYPE: DNA
<213> ORGANISM: Artificial sequence
<220> FEATURE:
<223> OTHER INFORMATION: A synthetic oligonucleotide PLAU ORF reverse
      sequence

<400> SEQUENCE: 32
gtggtgactt cagagccgta g                                              21

<210> SEQ ID NO 33
<211> LENGTH: 21
<212> TYPE: DNA
<213> ORGANISM: Artificial sequence
<220> FEATURE:
<223> OTHER INFORMATION: A synthetic oligonucleotide DIAPH1 forward
      primer

<400> SEQUENCE: 33
aggaagcatg agggcaacta t                                              21

<210> SEQ ID NO 34
<211> LENGTH: 21
<212> TYPE: DNA
<213> ORGANISM: Artificial sequence
<220> FEATURE:
<223> OTHER INFORMATION: A synthetic oligonucleotide DIAPH1 reverse
      primer
```

```
<400> SEQUENCE: 34
cccaggaata gtccaaagga g                                              21

<210> SEQ ID NO 35
<211> LENGTH: 21
<212> TYPE: DNA
<213> ORGANISM: Artificial sequence
<220> FEATURE:
<223> OTHER INFORMATION: A synthetic oligonucleotide DIAPH1 ORF forward
      primer

<400> SEQUENCE: 35
agctgccaca gatgaaaaag a                                              21

<210> SEQ ID NO 36
<211> LENGTH: 21
<212> TYPE: DNA
<213> ORGANISM: Artificial sequence
<220> FEATURE:
<223> OTHER INFORMATION: A synthetic oligonucleotide DIAPH1 ORF reverse
      sequence

<400> SEQUENCE: 36
tcttggggtc aaagaggaag t                                              21

<210> SEQ ID NO 37
<211> LENGTH: 21
<212> TYPE: DNA
<213> ORGANISM: Artificial sequence
<220> FEATURE:
<223> OTHER INFORMATION: A synthetic oligonucleotide EDEM1 forward
      primer

<400> SEQUENCE: 37
tgaaaaggta gggctgagtg a                                              21

<210> SEQ ID NO 38
<211> LENGTH: 21
<212> TYPE: DNA
<213> ORGANISM: Artificial sequence
<220> FEATURE:
<223> OTHER INFORMATION: A synthetic oligonucleotide EDEM1 reverse
      primer

<400> SEQUENCE: 38
gcagggaaga ggcactagaa t                                              21

<210> SEQ ID NO 39
<211> LENGTH: 21
<212> TYPE: DNA
<213> ORGANISM: Artificial sequence
<220> FEATURE:
<223> OTHER INFORMATION: A synthetic oligonucleotide RPIA forward primer

<400> SEQUENCE: 39
gagcggtatg gtatggaatg a                                              21

<210> SEQ ID NO 40
<211> LENGTH: 21
<212> TYPE: DNA
<213> ORGANISM: Artificial sequence
<220> FEATURE:
<223> OTHER INFORMATION: A synthetic oligonucleotide RPIA reverse primer

<400> SEQUENCE: 40
gcatttctgg tcaactgctt c                                              21
```

-continued

```
<210> SEQ ID NO 41
<211> LENGTH: 21
<212> TYPE: DNA
<213> ORGANISM: Artificial sequence
<220> FEATURE:
<223> OTHER INFORMATION: A synthetic oligonucleotide MYD88 forward
      primer

<400> SEQUENCE: 41
gcatgatctt gttgaggcat t                                              21

<210> SEQ ID NO 42
<211> LENGTH: 21
<212> TYPE: DNA
<213> ORGANISM: Artificial sequence
<220> FEATURE:
<223> OTHER INFORMATION: A synthetic oligonucleotide MYD88 reverse
      primer

<400> SEQUENCE: 42
atggcaaata tcggcttttc t                                              21

<210> SEQ ID NO 43
<211> LENGTH: 21
<212> TYPE: DNA
<213> ORGANISM: Artificial sequence
<220> FEATURE:
<223> OTHER INFORMATION: A synthetic oligonucleotide ICAM1 forward
      primer

<400> SEQUENCE: 43
gcactatgca gctccagttt c                                              21

<210> SEQ ID NO 44
<211> LENGTH: 21
<212> TYPE: DNA
<213> ORGANISM: Artificial sequence
<220> FEATURE:
<223> OTHER INFORMATION: A synthetic oligonucleotide ICAM1 reverse
      primer

<400> SEQUENCE: 44
caagactgca gtgaaccatg a                                              21

<210> SEQ ID NO 45
<211> LENGTH: 21
<212> TYPE: DNA
<213> ORGANISM: Artificial sequence
<220> FEATURE:
<223> OTHER INFORMATION: A synthetic oligonucleotide KRT14 forward
      primer

<400> SEQUENCE: 45
catgagtgtg gaagccgaca t                                              21

<210> SEQ ID NO 46
<211> LENGTH: 21
<212> TYPE: DNA
<213> ORGANISM: Artificial sequence
<220> FEATURE:
<223> OTHER INFORMATION: A synthetic oligonucleotide KRT14 reverse
      primer

<400> SEQUENCE: 46
gcctctcagg gcattcatct c                                              21
```

<210> SEQ ID NO 47
<211> LENGTH: 21
<212> TYPE: DNA
<213> ORGANISM: Artificial sequence
<220> FEATURE:
<223> OTHER INFORMATION: A synthetic oligonucleotide KHSRP forward
      primer

<400> SEQUENCE: 47
ctgttttgtt tggcgagaga g                                           21

<210> SEQ ID NO 48
<211> LENGTH: 21
<212> TYPE: DNA
<213> ORGANISM: Artificial sequence
<220> FEATURE:
<223> OTHER INFORMATION: A synthetic oligonucleotide KHSRP reverse
      primer

<400> SEQUENCE: 48
gagacacaga acaggcgaga g                                           21

<210> SEQ ID NO 49
<211> LENGTH: 21
<212> TYPE: DNA
<213> ORGANISM: Artificial sequence
<220> FEATURE:
<223> OTHER INFORMATION: A synthetic oligonucleotide HuR forward primer

<400> SEQUENCE: 49
ttgtaagtca ccgccagtac c                                           21

<210> SEQ ID NO 50
<211> LENGTH: 21
<212> TYPE: DNA
<213> ORGANISM: Artificial sequence
<220> FEATURE:
<223> OTHER INFORMATION: A synthetic oligonucleotide HuR reverse primer

<400> SEQUENCE: 50
tcacatggtc atggtcaaag a                                           21

<210> SEQ ID NO 51
<211> LENGTH: 21
<212> TYPE: DNA
<213> ORGANISM: Artificial sequence
<220> FEATURE:
<223> OTHER INFORMATION: A synthetic oligonucleotide RPLP0 forward
      primer

<400> SEQUENCE: 51
cagattggct acccaactgt t                                           21

<210> SEQ ID NO 52
<211> LENGTH: 21
<212> TYPE: DNA
<213> ORGANISM: Artificial primer
<220> FEATURE:
<223> OTHER INFORMATION: A synthetic oligonucleotide RPLP0 reverse
      primer

<400> SEQUENCE: 52
gggaaggtgt aatccgtctc c                                           21

<210> SEQ ID NO 53
<211> LENGTH: 31
<212> TYPE: DNA
<213> ORGANISM: Artificial sequence
<220> FEATURE:
<223> OTHER INFORMATION: A synthetic oligonucleotide DIAPH1 foward
      primer

<400> SEQUENCE: 53
tccagagctc ctaaggaagc agggagcaaa t                              31

<210> SEQ ID NO 54
<211> LENGTH: 31
<212> TYPE: DNA
<213> ORGANISM: Artificial sequence
<220> FEATURE:
<223> OTHER INFORMATION: A synthetic oligonucleotide DIAPH1 reverse
      primer

<400> SEQUENCE: 54
tccatctaga gcccacccac ttctctttta g                              31

<210> SEQ ID NO 55
<211> LENGTH: 30
<212> TYPE: DNA
<213> ORGANISM: Artificial sequence
<220> FEATURE:
<223> OTHER INFORMATION: A synthetic oligonucleotide LAMC2 forward
      primer

<400> SEQUENCE: 55
ccagagctcg ggtgtgagaa tgatcaagga                                30

<210> SEQ ID NO 56
<211> LENGTH: 30
<212> TYPE: DNA
<213> ORGANISM: Artificial sequence
<220> FEATURE:
<223> OTHER INFORMATION: A synthetic oligonucleotide LAMC2 reverse
      primer

<400> SEQUENCE: 56
ccatctagac ccagctgaag tgtgagtagg                                30

<210> SEQ ID NO 57
<211> LENGTH: 31
<212> TYPE: DNA
<213> ORGANISM: Artificial sequence
<220> FEATURE:
<223> OTHER INFORMATION: A synthetic oligonucleotide KHSRP forward
      primer

<400> SEQUENCE: 57
tccagagctc aggctcaatg aatcgaatga a                              31

<210> SEQ ID NO 58
<211> LENGTH: 31
<212> TYPE: DNA
<213> ORGANISM: Artificial sequence
<220> FEATURE:
<223> OTHER INFORMATION: A synthetic oligonucleotide PLAU reverse primer

<400> SEQUENCE: 58
tccatctaga gccccaggag tgacctataa c                              31

-continued

```
<210> SEQ ID NO 59
<211> LENGTH: 31
<212> TYPE: DNA
<213> ORGANISM: Artificial sequence
<220> FEATURE:
<223> OTHER INFORMATION: A synthetic oligonucleotide KSHRP forward
      primer

<400> SEQUENCE: 59
tccagagctc aggctcaatg aatcgaatga a                                    31

<210> SEQ ID NO 60
<211> LENGTH: 31
<212> TYPE: DNA
<213> ORGANISM: Artificial sequence
<220> FEATURE:
<223> OTHER INFORMATION: A synthetic oligonucleotide KSHRP reverse
      primer

<400> SEQUENCE: 60
tccatctaga tacaacacct ggtccaagga a                                    31

<210> SEQ ID NO 61
<211> LENGTH: 30
<212> TYPE: DNA
<213> ORGANISM: Artificial sequence
<220> FEATURE:
<223> OTHER INFORMATION: A synthetic oligonucleotide FSTL1 forward
      primer

<400> SEQUENCE: 61
ccagagctca tcccagcatc ttctccactt                                      30

<210> SEQ ID NO 62
<211> LENGTH: 29
<212> TYPE: DNA
<213> ORGANISM: Artificial sequence
<220> FEATURE:
<223> OTHER INFORMATION: A synthetic oligonucleotide FSTL1 reverse
      primer

<400> SEQUENCE: 62
ccatctagat aattggggga aaggaaacc                                       29

<210> SEQ ID NO 63
<211> LENGTH: 22
<212> TYPE: DNA
<213> ORGANISM: Artificial sequence
<220> FEATURE:
<223> OTHER INFORMATION: A synthetic oligonucleotide miR-198 in situ
      hybridisation probe

<400> SEQUENCE: 63
gaacctatct cccctctgga cc                                              22

<210> SEQ ID NO 64
<211> LENGTH: 22
<212> TYPE: DNA
<213> ORGANISM: Artificial sequence
<220> FEATURE:
<223> OTHER INFORMATION: A synthetic oligonucleotide scrambeled in situ
      hybridisation, exiqon

<400> SEQUENCE: 64
gtgtaacacg tctatacgcc ca                                              22
```